US012390546B2

(12) United States Patent
Ludowise et al.

(10) Patent No.: US 12,390,546 B2
(45) Date of Patent: Aug. 19, 2025

(54) STERILIZATION INDICATOR READING APPARATUS WITH A COLOR SENSOR

(71) Applicant: Solventum Intellectual Properties Company, Maplewood, MN (US)

(72) Inventors: Peter D. Ludowise, Cottage Grove, MN (US); Anthony J. Jennen, Vadnais Heights, MN (US); Barry W. Robole, Hudson, WI (US); Leroy J. Longworth, Woodbury, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 971 days.

(21) Appl. No.: 17/310,654

(22) PCT Filed: Mar. 13, 2020

(86) PCT No.: PCT/IB2020/052318
§ 371 (c)(1),
(2) Date: Aug. 16, 2021

(87) PCT Pub. No.: WO2020/183433
PCT Pub. Date: Sep. 17, 2020

(65) Prior Publication Data
US 2021/0402033 A1    Dec. 30, 2021

Related U.S. Application Data

(60) Provisional application No. 62/818,344, filed on Mar. 14, 2019.

(51) Int. Cl.
*A61L 2/28*    (2006.01)
*C12M 1/12*    (2006.01)
(Continued)

(52) U.S. Cl.
CPC .............. *A61L 2/28* (2013.01); *C12M 37/06* (2013.01); *C12Q 1/22* (2013.01); *G01N 21/6428* (2013.01);
(Continued)

(58) Field of Classification Search
CPC ................................. A61L 2/28; C12M 37/06
See application file for complete search history.

(56) References Cited

U.S. PATENT DOCUMENTS

| 5,073,488 A | 12/1991 | Matner |
| 5,223,401 A | 6/1993 | Foltz |
| 5,418,167 A | 5/1995 | Matner |
| 5,770,393 A | 6/1998 | Dalmasso |

(Continued)

FOREIGN PATENT DOCUMENTS

| CN | 204625632 | 9/2015 | |
| WO | WO-2012061228 A1 * | 5/2012 | ............... A61L 2/28 |
| WO | 2013122852 A1 | 8/2013 | |

OTHER PUBLICATIONS

International Search Report for PCT International Application No. PCT/IB2020/052318, mailed on Jun. 16, 2020, 4 pages.

*Primary Examiner* — Elizabeth A Robinson
*Assistant Examiner* — Jonathan E Lepage

(57) ABSTRACT

Aspects of the present disclosure relate to a reading apparatus that a well formed from a portion of a housing. The well dimensioned to receive at least a portion of a sterilization indicator having spores. The reading apparatus can also have a heating element thermally coupled to a portion of the well and an excitation source to excite the substance in the sterilization indicator. The reading apparatus can have a sterilization indicator activation circuit for detecting activation of the sterilization indicator. The excitation source is positioned such that light from the excitation source is (Continued)

directed into the well. A color sensor can be positioned adjacent the well to receive reflected light from the sterilization indicator.

19 Claims, 15 Drawing Sheets

(51) Int. Cl.
  *C12Q 1/22* (2006.01)
  *G01N 21/64* (2006.01)
  *H05K 1/18* (2006.01)

(52) U.S. Cl.
  CPC ..... *H05K 1/181* (2013.01); *G01N 2021/6439* (2013.01); *G01N 2201/0484* (2013.01); *G01N 2201/062* (2013.01); *H05K 2201/10106* (2013.01); *H05K 2201/10151* (2013.01)

(56) References Cited

U.S. PATENT DOCUMENTS

| | | |
|---|---|---|
| 5,863,790 A | 1/1999 | Bolea |
| 6,025,189 A | 2/2000 | Bolea |
| 6,063,591 A | 5/2000 | Bolea |
| 9,303,283 B2 | 4/2016 | Franciskovich |
| 9,410,180 B2 | 8/2016 | Pederson |
| 10,161,873 B2 | 12/2018 | Luo et al. |
| 2003/0133830 A1 | 7/2003 | Gonzalez |
| 2003/0165398 A1* | 9/2003 | Waldo ............... A61L 2/087 604/20 |
| 2004/0197848 A1 | 10/2004 | Behun |
| 2006/0263258 A1* | 11/2006 | Harris ............... A61L 2/28 422/400 |
| 2013/0210069 A1 | 8/2013 | Pederson |
| 2013/0273594 A1 | 10/2013 | Ahimou et al. |
| 2014/0242717 A1* | 8/2014 | Rochette ......... G01N 21/6486 422/69 |
| 2015/0147773 A1 | 5/2015 | Franciskovich |
| 2015/0337354 A1 | 11/2015 | Ahimou et al. |

\* cited by examiner

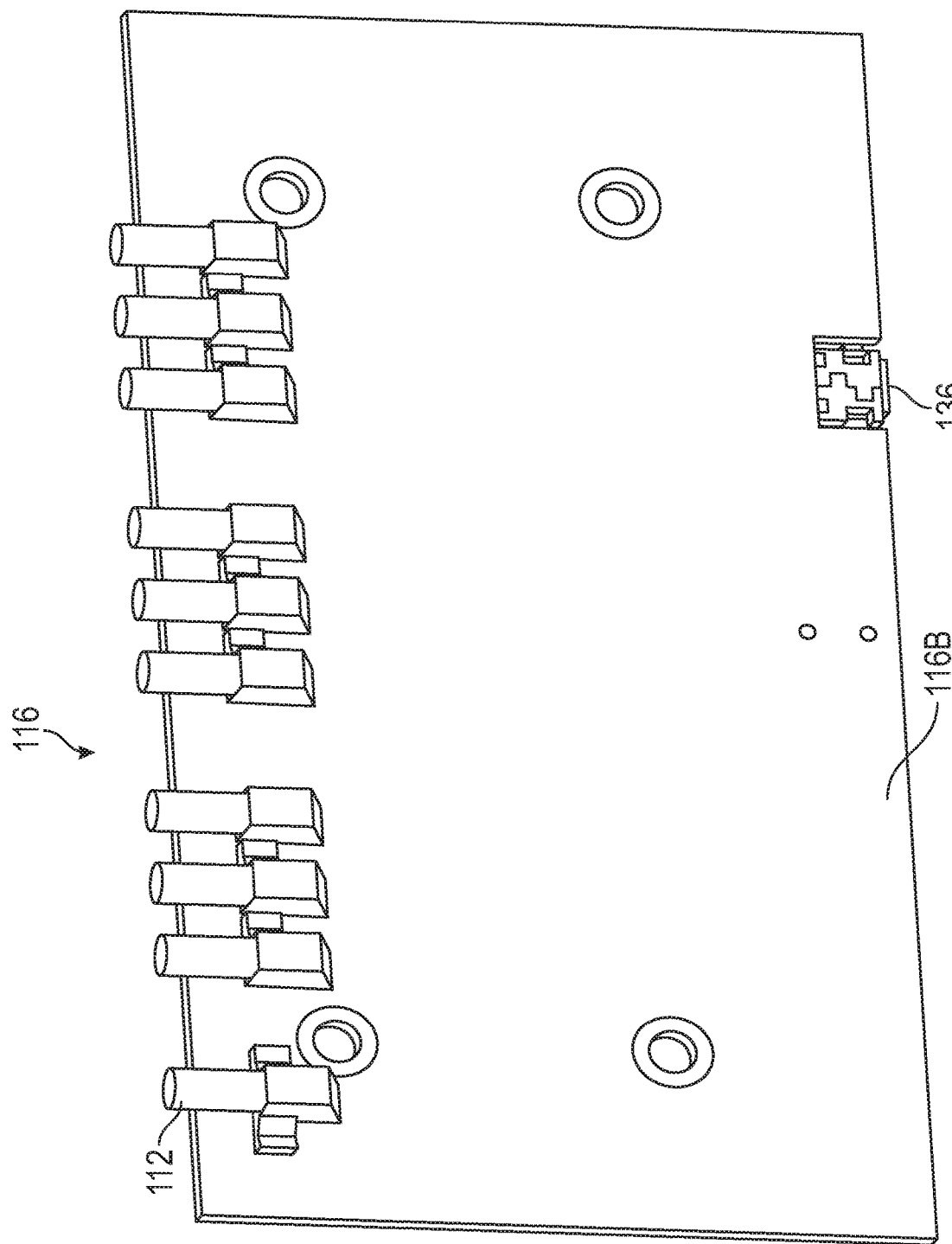

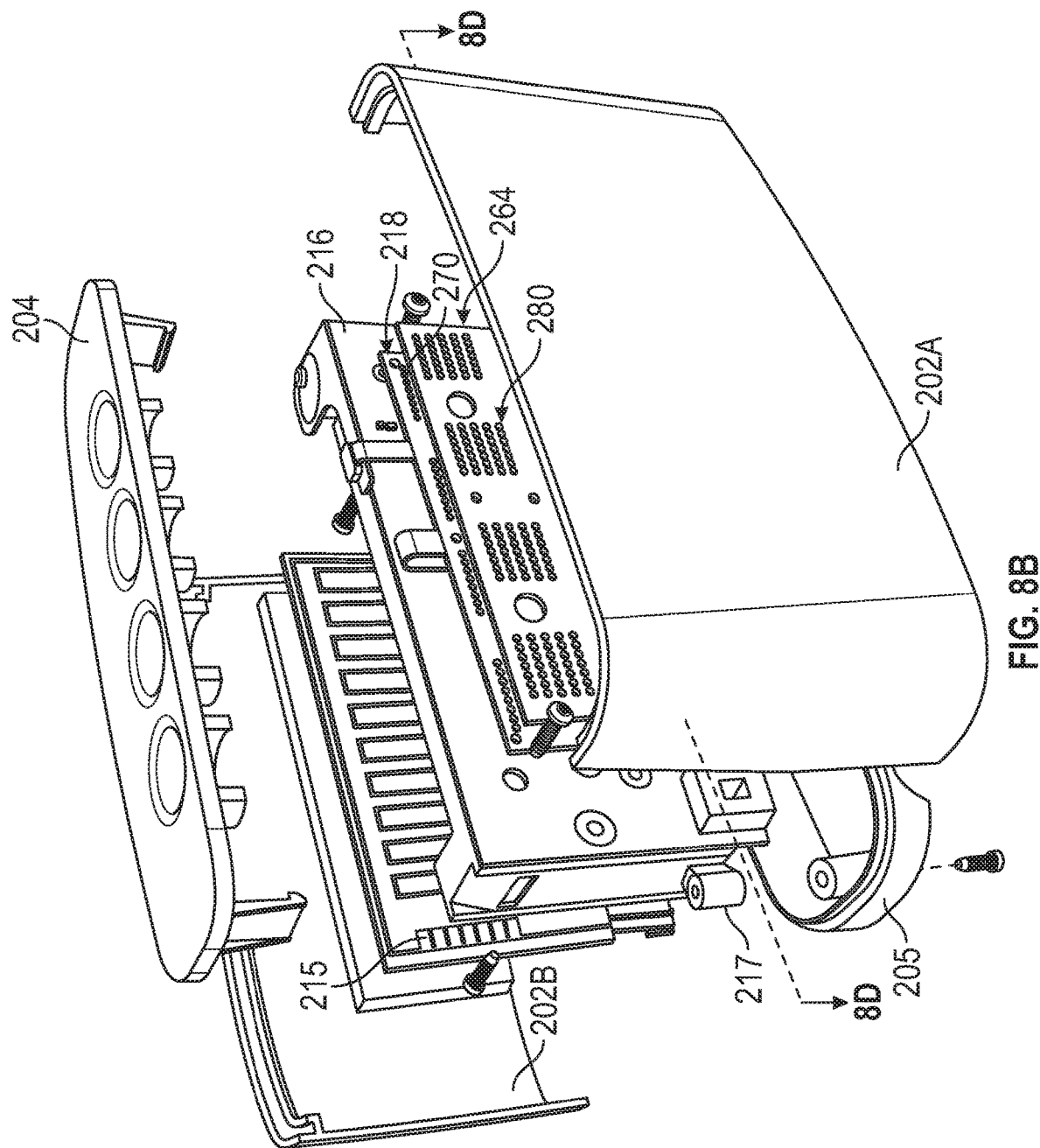

STERILIZATION INDICATOR READING APPARATUS WITH A COLOR SENSOR

CROSS REFERENCE TO RELATED APPLICATIONS

This application is a national stage filing under 35 U.S.C. 371 of PCT/IB2020/052318 filed Mar. 13, 2020, which claims the benefit of U.S. Provisional Application No. 62/818,344, filed Mar. 14, 2019, the disclosure of which is incorporated by reference in its/their entirety herein.

BACKGROUND

In a variety of industries, such as the health care industry but also in other industrial applications, it can be necessary to monitor the effectiveness of processes used to sterilize equipment such as medical devices, instruments and other disposable and non-disposable articles. In these settings, a sterilization cycle is generally defined as the process of completely destroying all viable sources of biological activity, such as microorganisms, including structures such as viruses and spores. As a standard practice, hospitals include a sterilization indicator with a batch of articles to assay the lethality of the sterilization process. Both biological and chemical sterilization indicators have been used.

One standard type of biological sterilization indicator includes a known quantity of test microorganisms, for example *Geobacillus stearothermophilus* (formerly *Bacillus stearothermophilus*) or *Bacillus atrophaeus* (formerly *Bacillus subtilis*) spores, which can be many times more resistant to particular sterilization processes than other contaminating organisms. After the indicator is exposed to the sterilization process, the sources of biological activity (e.g., spores) can be incubated in a liquid nutrient medium to determine whether any of the sources survived the sterilization process, with source metabolism and/or growth indicating that the sterilization process was insufficient to destroy all of the sources of biological activity.

Available chemical sterilization indicators can be read immediately at the end of the sterilization process. However, the results indicate only that a particular condition was present during the sterilization process, such as the presence of a particular chemical or a temperature, and potentially, that the condition was reached for a certain period of time. On the contrary, the response of sources of biological activity to all conditions actually present can be a more direct and reliable test for how effective a sterilization process is in achieving sterilization.

Some reading apparati for determining sterility of sterilization indicators are described in U.S. Pat. No. 9,410,180, which is incorporated by reference, utilize a photodiode to determine the fluorescent response of spores. The photodiode may employ the use of filters which can make manufacturability difficult and expensive.

Further, some reading apparati can also have multiple printed circuit boards that are arranged in various configurations which can add complexity and cost to a reading apparatus.

SUMMARY

Aspects of the present disclosure relate to a reading apparatus that has a housing comprising a top portion, a bottom portion, and a major side portion. The reading apparatus can have a well formed from a portion of the housing, accessible from the top portion, and oriented along a well axis from the top portion to the bottom portion. The well dimensioned to receive at least a portion of a sterilization indicator having spores and a substance fluorescently responsive to spore concentration and the spores are responsive to an environmental condition in a sterilizer.

The reading apparatus can also have a heating element thermally coupled to a portion of the well and an excitation source to excite the substance in the sterilization indicator. The reading apparatus can have a sterilization indicator activation circuit for detecting activation of the sterilization indicator. The excitation source is positioned such that light from the excitation source is directed into the well. A color sensor can be positioned adjacent the well to receive reflected light from the sterilization indicator and detect activation of the sterilization indicator. The reading apparatus can include a controller circuit comprising: a processor, a memory communicatively coupled to the processor. The heating element, excitation source, the color sensor, and sterilization indicator activation circuit are communicatively coupled to the processor.

Another aspect of the present disclosure is that the reading apparatus comprises a first printed circuit board having the excitation source, color sensor, and controller circuit disposed thereon, preferably surface mounted. The first printed circuit board forms a first plane that is oriented parallel with the well axis and the parallel orientation is maintained by the housing.

BRIEF DESCRIPTION OF DRAWINGS

FIG. 2A-2B illustrate a printed circuit board having the excitation source, color sensor, and sterilization indicator activation detection circuit disposed thereon, according to various embodiments.

FIG. 8B illustrates another exploded view of the reading apparatus of FIG. 8A.

DETAILED DESCRIPTION

Aspects of the present disclosure relate to a sterilization indicator reading apparatus having a compact housing. Aspects of the present disclosure also include using a color sensor to detect fluorescence of the sterilization indicator. For example, using a low cost color sensor to read not only a fluorescence detection cycle but also verify that the sterilization indicator is activated. Additional aspects of the present disclosure relate to a display of the reading apparatus illuminating through a major side portion of the housing and being visible from at least 10 feet away.

Figure 1A:
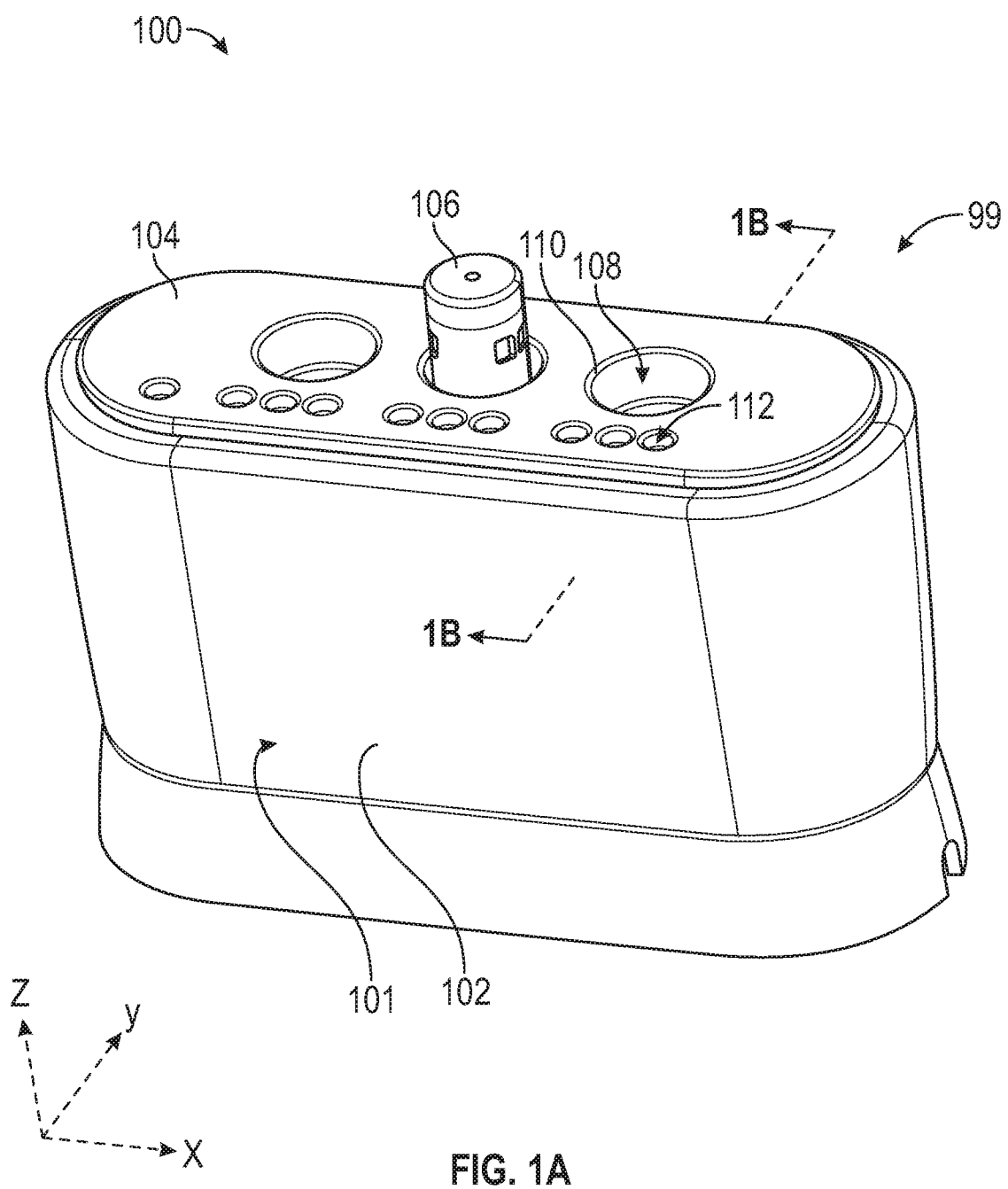
FIG. 1A illustrates a system including a reading apparatus with a sterilization indicator disposed within the reading apparatus, according to various embodiments.

FIG. 1 illustrates a system 99 that includes a sterilization indicator 106 and a sterilization indicator reading apparatus 100 according to at least one embodiment. The reading apparatus 100 can seat a plurality of sterilization indicators within a plurality of wells with one well (e.g., 108) being described in detail.

The reading apparatus 100 can include a housing 101. The housing 101 is compact, meaning that the housing 101 has an internal volume of no greater than 0.5 L, no greater than 0.4 L, no greater than 0.3 L, or no greater than 0.2 L. The housing 101 is shown as being mostly rectangular, when viewed from a top to bottom direction (i.e., a z dimension), has a rounded rectangular or an ellipsoidal cross-section. The housing 101 can have a x-dimension formed along the major side portion 102 and a y-dimension formed along a minor side portion.

The housing 101 has two straight edges and two cured edges. The straight edge can be the major side portion 102. The housing 101 can also have a top portion 104. The top portion 104 can be where a sterilization indicator 106 is inserted. The top portion 104 can be flush with an edge of a major side portion 102 but is shown extending above the plane of the major side portion 102. The top portion 104 can have a plurality of holes 110 leading to a plurality of wells 108. The reading apparatus 100 illustrates at least three wells arranged in a linear configuration along the x-dimension.

Each well 108 can be formed from a hole 110 and is accessible from the top portion 104 by a sterilization indicator 106. In at least one embodiment, the well 108 has a depth defined by the sterilization indicator 106. The well 108 can have an orientation along the z-dimension that allows a liquid nutrient medium (which may also be described as a medium) to collect at the base of the sterilization indicator 106 (preferably through gravity) when a frangible container containing the medium is broken. For example, the well 108 orientation is vertical along the z-dimension and perpendicular to a plane formed by the top portion 104 or bottom portion (105 on FIG. 1B). In at least one embodiment, the well 108 can be askew from the vertical axis of the reading apparatus 100.

Each sterilization indicator 106 can be dimensioned to be received by the well 108. For example, the sterilization indicator 106 can have one or more features that allow the sterilization indicator 106 to be keyed relative to the well 108 such as a shelf, protrusion, or body shape.

The sterilization indicator 106 is preferably a biological sterilization indicator (e.g., self-contained biological sterilization indicator) and uses spores to evaluate a sterilization cycle from a sterilizer. For example, the sterilization indicator 106 can be placed in a sterilization cycle of the sterilizer, then the spores can be exposed to the medium to propagate. For example, the sterilization indicator 106 can use an α-glucosidase enzyme system, which is generated naturally within growing cells of *Geobacillus stearothermophilus*. The α-glucosidase in its active state is detected by measuring the fluorescence produced by the enzymatic hydrolysis of a substance (e.g., a non-fluorescent substrate, 4-methylumbelliferyl-α-D-glucoside (MUG)).

The spores used in a particular system are selected according to the sterilization process used. For example, for a steam sterilization process, *Geobacillus stearothermophilus* or *Bacillus stearothermophilus* can be used. In another example, for an ethylene oxide sterilization process, *Bacillus atrophaeus* (formerly *Bacillus subtilis*) can be used. In some embodiments, the sterilization process resistant spores can include, but are not limited to, at least one of *Geobacillus stearothermophilus*, *Bacillus stearothermophilus*, *Bacillus subtilis*, *Bacillus atrophaeus*, *Bacillus megaterium*, *Bacillus coagulans*, *Clostridium sporogenes*, *Bacillus pumilus*, or combinations thereof.

Enzymes and substrates that can be suitable for use in the biological sterilization indicator of the present disclosure are identified in U.S. Pat. No. 5,073,488 (Matner et al), U.S. Pat. No. 5,418,167 (Matner et al.), and U.S. Pat. No. 5,223,401 (Foltz et al.), which are incorporated herein by reference for all they disclose.

The nutrient medium (preferably liquid) can generally be selected to induce germination and initial outgrowth of the spores, if viable. The nutrient medium can include one or more sugars, including, but not limited to, glucose, fructose, cellibiose, or the like, or a combination thereof. The nutrient medium can also include a salt, including, but not limited to, potassium chloride, calcium chloride, or the like, or a combination thereof. In some embodiments, the nutrient can further include at least one amino acid, including, but not limited to, at least one of methionine, phenylalanine, and tryptophan.

Generally, the sterilization indicator 106 has spores and a substance fluorescently responsive to the spore concentration and the spores are responsive to an environmental condition in a sterilizer. A low propagation of spores during an incubation cycle or fluorescence detection cycle can be indicative of low microbial concentration and an effective sterilization cycle. Examples of biological sterilization indicators are known and are manufactured by companies such as 3M under the trade designation ATTEST, Steris (Mentor, OH) under the trade designation Verify, and Terragene (Argentina).

While multiple configurations exist, the microbial spores are generally present in a spore carrier toward the base of the sterilization indicator 106, opposite from a cap. 3M (St Paul, MN) has been particularly innovative in a self-contained biological indicator configuration having at least one flat face (or major surface) as found in models 1295, 1491, and 1492V.

For example, the biological indicator includes an indicator housing including, a first portion, and a second portion adapted to be coupled to the first portion, the second portion being movable with respect to the first portion, when coupled to the first portion between a first position and a second position; and a container containing a liquid nutrient medium and being dimensioned to be positioned in the indicator housing, at least a portion of the container being frangible, the container having a first state in which the container is intact when the second portion of the indicator housing is in the first position, and a second state in which the container is fractured when the second portion of the indicator housing is in the second position.

In at least one embodiment, the sterilization indicator 106 has at least one indicator chamber. If there is one indicator chamber, then the indicator chamber can be uniform (e.g., a cylinder with planar walls) and have an upper portion and a lower portion housing the spores. In a uniform configuration, the location of the spores can mark the boundary between the lower portion and the upper portion. In a non-uniform configuration, e.g., at least one sloping wall and one straight wall, the upper portion can taper into a lower portion (which houses the spores). Thus, in a non-uniform configuration, the boundary between the upper and lower portions can be distinguished by a start of the slopped wall.

In at least one embodiment of a non-uniform configuration, the indicator chamber can further be divided into a first indicator chamber and a second indicator chamber. A first indicator chamber can exist within the indicator housing in which the container is positioned when the container is in the first state. A second indicator chamber can exist within the indicator housing in which the container and the liquid are not positioned when the container is in the first state, and into which the liquid moves when the container is in the second state, the second indicator chamber comprising at least one source of biological activity (i.e., microbial spores) that is not in fluid communication with the liquid when the container is in the first state and that is in fluid communication with the liquid when the container is in the second state. The indicator housing of the biological indicator can also include at least one substantially planar outer wall positioned adjacent the second indicator chamber of the indicator housing.

The housing 101 can have one or more indicator lights 112 for each well 108. The indicator lights 112 are shown as originating from within the housing 101. For example, the indicator lights 112 are visible through holes within the housing 101. In another embodiment, the indicator lights 112 can have visible to a user through the housing itself (i.e., through a thinner portion of housing 101 such as the top portion 104). The indicator lights 112 can provide information regarding one or more features of the reading apparatus 100. For example, a first indicator LED can indicate that a heating element is activated and a second indicator LED can indicate whether a second (preset) temperature has been achieved.

Figure 1B:
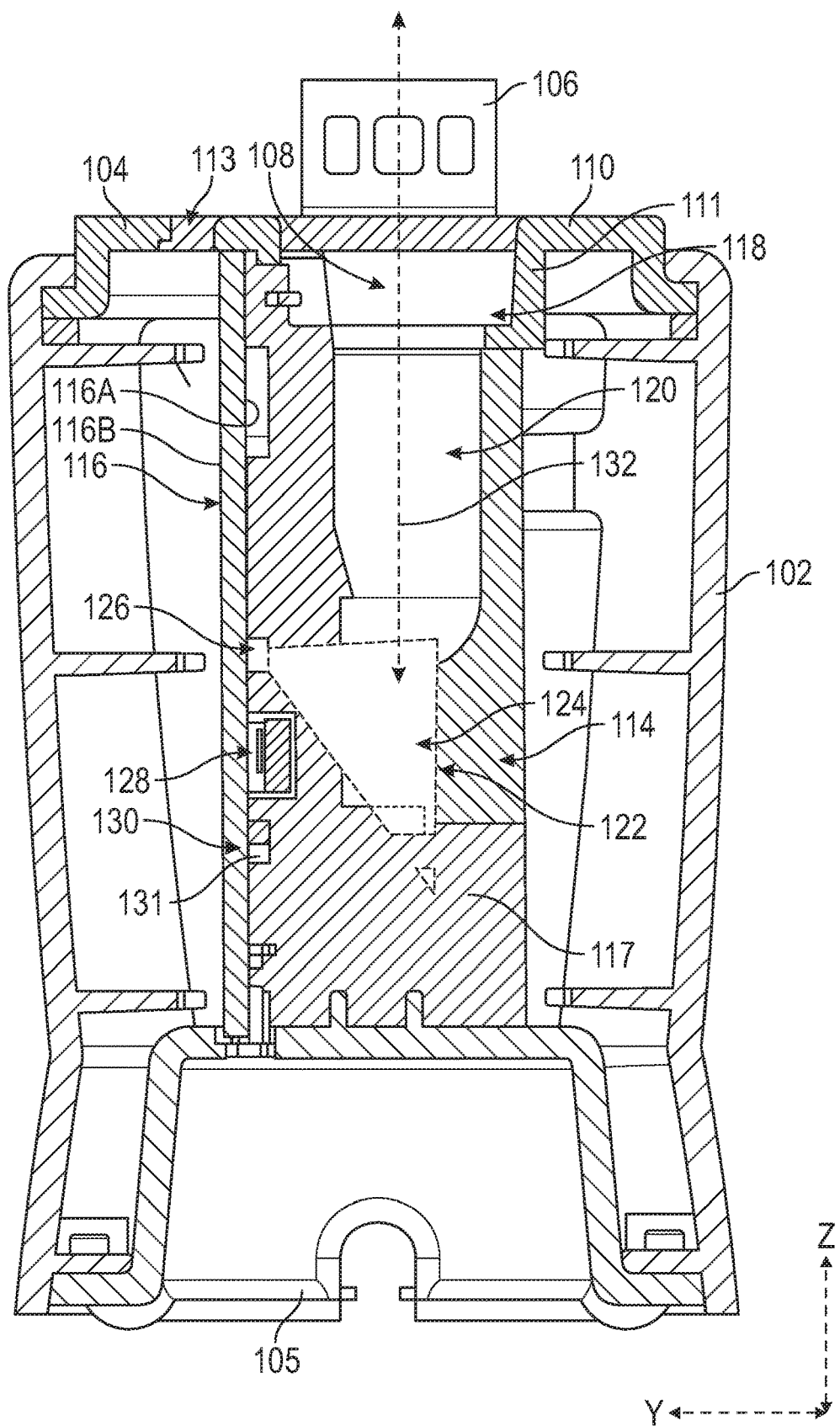
FIG. 1B illustrates a cross-sectional view along lines 1B-1B of the reading apparatus of FIG. 1A, according to various embodiments.

FIG. 1B illustrates a cross-section of the reading apparatus 100. The reading apparatus 100 can include a heater block 114, a spacing device 117, and a printed circuit board 116.

The heater block 114 is preferably at least partially formed from a thermally conductive material such as metals (e.g., steel, copper, aluminum), thermally conductive polymers, ceramics, or combinations thereof (including overlaid over non-thermally conductive polymers). In at least one embodiment, the heater block 114 can be non-thermally conductive and formed from polymeric materials. The heater block 114 distributes heat from a heating element (not shown) to the sterilization indicator 106 at a preset temperature and forms a portion of the well 108.

The heater block 114 itself can be optional. The heating element (not shown) is thermally coupled to the heater block 114. In at least one embodiment, the heating element can apply heat directly to the sterilization indicator 106. The heating element can have a temperature sensor that is embedded or thermally coupled to the heater block 114. The temperature sensor ensures that the heat applied to the sterilization indicator 106 is a preset temperature in a closed-loop heating system. The heating element can be activated or deactivated based on achieving the preset temperature. In at least one embodiment, the preset temperature can be 54±1 degrees Celsius or 60±1 degrees Celsius. In at least one embodiment, a plurality of heater blocks can exist in the reading apparatus 100 such that multiple preset temperatures can be used.

The spacing device 117 can maintain positioning and alignment between electronic elements on the printed circuit board 116 and the sterilization indicator 106 or the heater block 114. The spacing device 117 is formed from a rigid material such as polycarbonate or metal. In at least one embodiment, the spacing device 117 is formed from a light absorbing or non-reflective material to minimize interference by ambient light with a color sensor. For example, the spacing device 117 can have a matte finish so as not to reflect light. The spacing device 117 can also be black or gray in color. Thus, the spacing device can have a reflectivity no greater than 10 percent, or no greater than 5 percent from 400 nm to 700 nm using a calibrated reflectance meter commercially available as model Exact from X-Rite, Inc. (Grand Rapids, MI). In at least one embodiment, the spacing device 117 is mechanically coupled to a portion of the heater block 114 and/or the printed circuit board 116. The spacing device 117 is shown as adjacent to a base portion of the heater block 114. In at least one embodiment, the spacing device 117 aligns the sterilization indicator 106 with the heater block and forms a portion of the well 108.

The well 108 can be formed from both the heater block 114 and the spacing device 117. The well 108 is dimensioned to fit a sterilization indicator 106 and may have features that are responsive (i.e., keyed) to the sterilization indicator 106 such that the sterilization indicator is positioned fully within the well 108 in only one orientation.

In at least one embodiment, the well 108 includes and is bordered by the walls 111 of the top portion 104 that form the hole 110. Each well 108 can have different form factors to accommodate different types of sterilization indicators 106. For example, a first well can be keyed to fit an ethylene oxide biological indicator and provide a first preset temperature while a second well can be keyed to fit a biological indicator and provide a second preset temperature. In this example, the first preset temperature is different than a second preset temperature (e.g., different indicator types).

The well 108 can have a lip portion 118 which can support a portion of the sterilization indicator 106. The lip portion 118 can be formed from a portion of the wall 111 and keyed to the sterilization indicator 106. The wall 111 can further be configured in such a way to block ambient light from the environment. For example, a flexible portion such as foam disposed on the wall 111 can further block ambient light from reaching the color sensor.

The well 108 can be keyed to tapering sterilization indicators 106. In at least one embodiment, the well 108 can have a first (e.g., upper) chamber 120 and a second (e.g., lower) chamber 122 (which is partially obscured by optical path 124). The first chamber 120 can support the larger diameter of an upper portion of the sterilization indicator 106. The second chamber 122 can accommodate the smaller diameter of a lower (i.e., tapering) portion of the sterilization indicator 106. The second chamber can have a smaller perimeter than a perimeter of the first chamber (measured from the smallest perimeter of the corresponding portion of the sterilization indicator 106). In at least one embodiment, the second chamber 122 can be proximate to a spore location (e.g., a spore carrier) of the sterilization indicator 106. In at least one embodiment, the heating element can be proximate to the second chamber 122 of the well such that the spores and medium are heated locally.

The second chamber 122 can also form an optical path 124 from excitation source 126 to an indicator chamber (i.e., containing the spores) of the sterilization indicator 106. Fluorescent output from the indicator chamber can be further received by the color sensor 128.

In at least one embodiment, the well 108 can have a well axis 132 in the z-dimension. Thus, the well axis 132 can be alighted vertically from the top portion from top portion 104 to a bottom portion 105 (e.g., aligned with the z-dimension). The well axis 132 can further be representative of the alignment of the sterilization indicator 106. The well axis 132 can be parallel to the plane of the printed circuit board 116. Thus, the well axis 132 is not perpendicular to plane of the printed circuit board 116. If two or more wells are arranged linearly across the x-dimension to form a plane intersecting well axis 132 across at least two wells, this plane can also be parallel to the plane of the printed circuit board 116. In at least one embodiment, the printed circuit board 116 has a plane that is substantially parallel (meaning within 5 degrees) to a plane of the major side portion 102.

In at least one embodiment, the printed circuit board 116 can have the excitation source 126, a color sensor 128, and an activation detection circuit 130 disposed thereon. Each well can include a separate excitation source 126, a color sensor 128, and an activation detection circuit 130. In at least one embodiment, the printed circuit board 116 is continuous such that the excitation source 126, a color sensor 128, and an activation detection circuit 130 of a first well is on the same printed circuit board as the excitation source 126, a color sensor 128, and an activation detection circuit 130 as a second well. The printed circuit board 116 can be arranged such that it is parallel to the well axis 132.

Figure 2A:
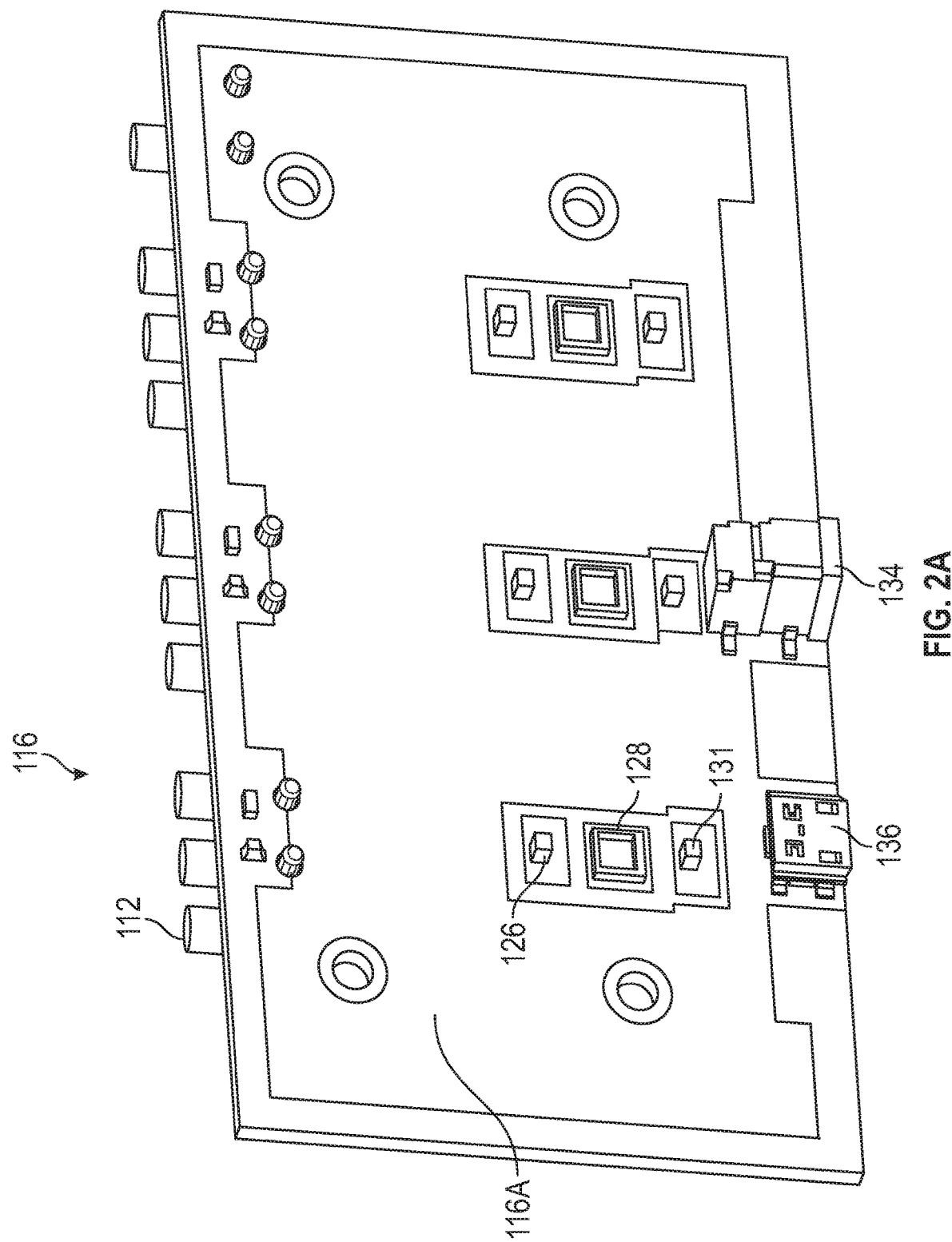

FIGS. 2A-2B illustrate the printed circuit board 116 in greater detail. While the printed circuit board 116 is preferably rigid and planar, the printed circuit board 116 can also be flexible.

In FIG. 2A, the printed circuit board 116 has a first side 116A and a second side 116B. The excitation source 126 can be disposed on the first side 116A by surface mounting the excitation source to the first side 116A. The excitation source 126 can be any source that causes a component of the sterilization indicator 106 to fluoresce. The excitation source 126 can be further configured to illuminate the growth area of the portion of the sterilization indicator 106 with the spore carrier.

The excitation source 126 can produce ultraviolet (UV) electromagnetic radiation. In at least one embodiment, UV can include wavelengths from 10 nanometers (nm) to 400 nanometers. However, wavelengths between 100 and 280 nm (i.e., UV-C) may be germicidal and interfere with the growth of spores. Thus, preferred wavelengths produced by the excitation source are 300 nm and 400 nm, and more preferably 365 nm.

While the excitation source 126 can be any device that produces UV light, such as incandescent bulbs, lasers (which can further focus the UV light onto the spore carrier), light emitting diodes (LEDs), the preferred excitation source 126 is one or more LEDs.

The printed circuit board 116 can also have a sterilization indicator activation detection circuit 130 disposed on the first side 116A. For example, the sterilization indicator activation detection circuit 130 can be a flush mounted to the first side 116A thereon. The activation detection circuit 130 can detect when the sterilization indicator 106 is activated (i.e., medium is mixed with the spores). In at least one embodiment, the activation detection circuit 130 can determine whether the medium is mixed with the spores by cap position, optical transmittance of the second portion, reflectance of the medium, a camera system to determine medium presence, electrode sensing of the medium, or even a mechanical or electrical button pressed by the user to confirm that the user activated the sterilization indicator 106. As an example, the activation detection circuit 130 detects a color change, in particular, a color change from empty to the color of the medium (e.g., purple).

The activation detection circuit 130 can have a light source such as a laser or LED 131. In at least one embodiment, LED 131 is white in color. The white LED 131 positioned such that light from LED 131 is directed into the well 108 and reflected light that originates from the LED 131 is received by the color sensor 128. Although various mounting options exist, the LED 131 is mounted offset from the color sensor 128 such that light from the LED 131 is capable of illuminating the second chamber of the well. As shown, the color sensor 128 is mounted between the excitation source side 116A and LED 131.

In another configuration, a plurality of LEDs can be surface mounted to the printed circuit board 116A and arranged around the perimeter of the color sensor 128. The light from the excitation source can form a 20 degree angle with the color sensor 128 when reflected from the sterilization indicator 106.

The activation detection circuit 130 can also include the color sensor 128. In at least one embodiment, the color sensor 128 can be independent from the activation detection circuit 130. For example, if the activation detection circuit 130 is based on a press button to confirm activation, then the color sensor 128 can receive light only originating from the excitation source 126. As shown, the color sensor 128 is electrically coupled to and receives light originating from both the excitation source 126 and LED 131. Thus, the color sensor 128 can be shared between the activation detection circuit 130 and the excitation source 126.

The color sensor 128 can be a RGB color sensor. Examples of RCB colors sensors are commercially available from Vishay model number VEML6040 or Hamamatsu model number S9702. The color sensor 128 can detect both fluorescence from microbial activity and whether there is growth media in the housing of the sterilization indicator 106. For example, the controller circuit can detect (based on readings from the color sensor 128) 1) the sterilization indicator 106 being positioned in the well 108 with the medium being present or not being present in the sterilization indicator 106.

The color sensor 128 can also be surface mounted on the first side 116A. The color sensor 128 can be aligned with the second chamber 122 (if the well 108 is multichambered). For example, the color sensor 128 is positioned adjacent a region of the well 108 dimensioned to receive at least a portion of the sterilization indicator 106 having a spore carrier. In at least one embodiment, the color sensor 128 is horizontally aligned with a portion of the spore carrier. For example, a horizontal axis (defined by an axis perpendicular to axis 132 of the spore carrier) can be about the same level as a spore carrier of an sterilization indicator 106. The fluorescent activity resulting from spores can be illuminated by the excitation source 126 and received by the color sensor 128. In at least one embodiment, the color sensor 128 and excitation source 126 are vertically aligned along the well axis. A second color sensor, second excitation source can also vertically aligned with another well having a second well axis. In another embodiment, the color sensor 128, excitation source 126, and the LED 131 can be vertically aligned.

In at least one embodiment, the color sensor 128 can have a long pass filter disposed thereon. The long pass filter can be 435 nm. The long pass filter can prevent interference from the excitation source 126 and/or ambient light sources.

Figure 8A:
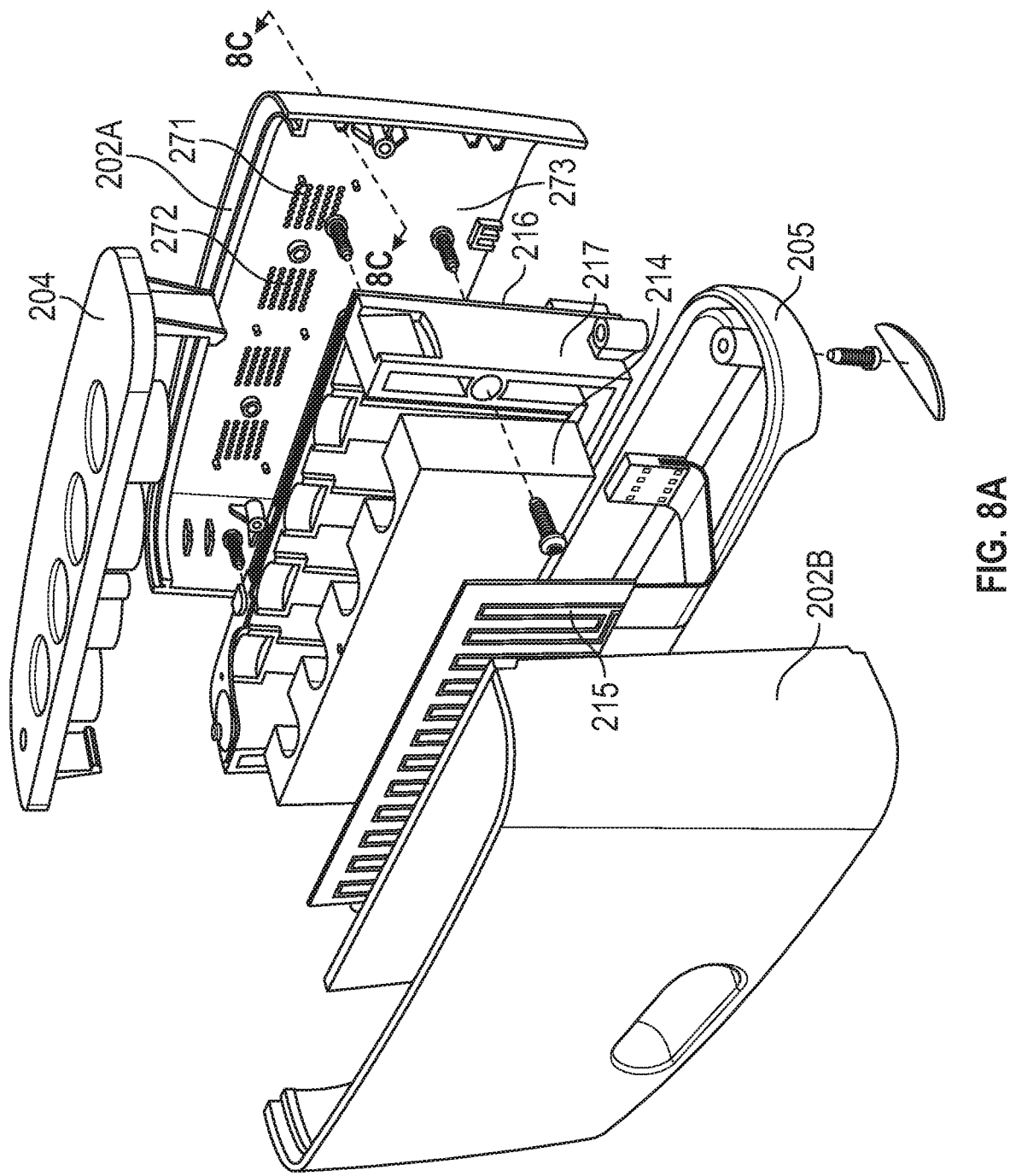
FIG. 8A illustrates a exploded view of various components of the reading device of FIG. 7.
Figure 8C:
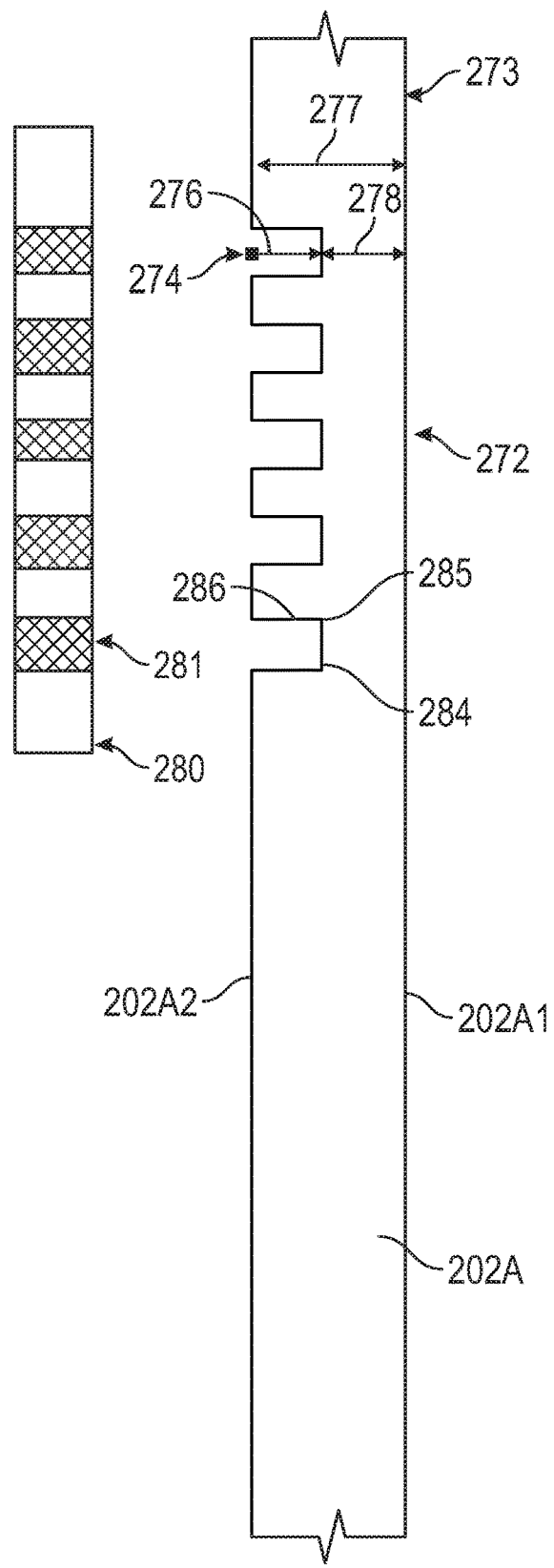
FIG. 8C illustrates a cross-sectional view of the major side portion of FIG. 8A along lines 8C-8C, according to various embodiments.

The printed circuit board 116 can also have a heater element similar to that described in FIG. 8. The heater element can be a flexible circuit electrically coupled to the printed circuit board 116 for power and the heater element can also be thermally and mechanically coupled to the heater block 114 itself (e.g., on the side opposite the well).

Indicator lights 112 can include light pipes mounted at a right angle to the printed circuit board 116 as shown on FIG. 2B. In addition, the printed circuit board 116 can have a power port 134 that receives power to the reading apparatus 100. The power port 134 can be externally facing and include a 12V power jack. In at least one embodiment, the power port 134 can lead to an internal battery having a power capacity of at least 4000 mAh. The printed circuit board 116 can also include a communication port 136. As shown, the communication port 136 utilizes the universal serial bus standard and can couple to the controller circuit. The communication port 136 can allow an external computer to obtain history for each sterilization indicator 106, firmware update, external control of functions, or combinations thereof.

Figure 7:
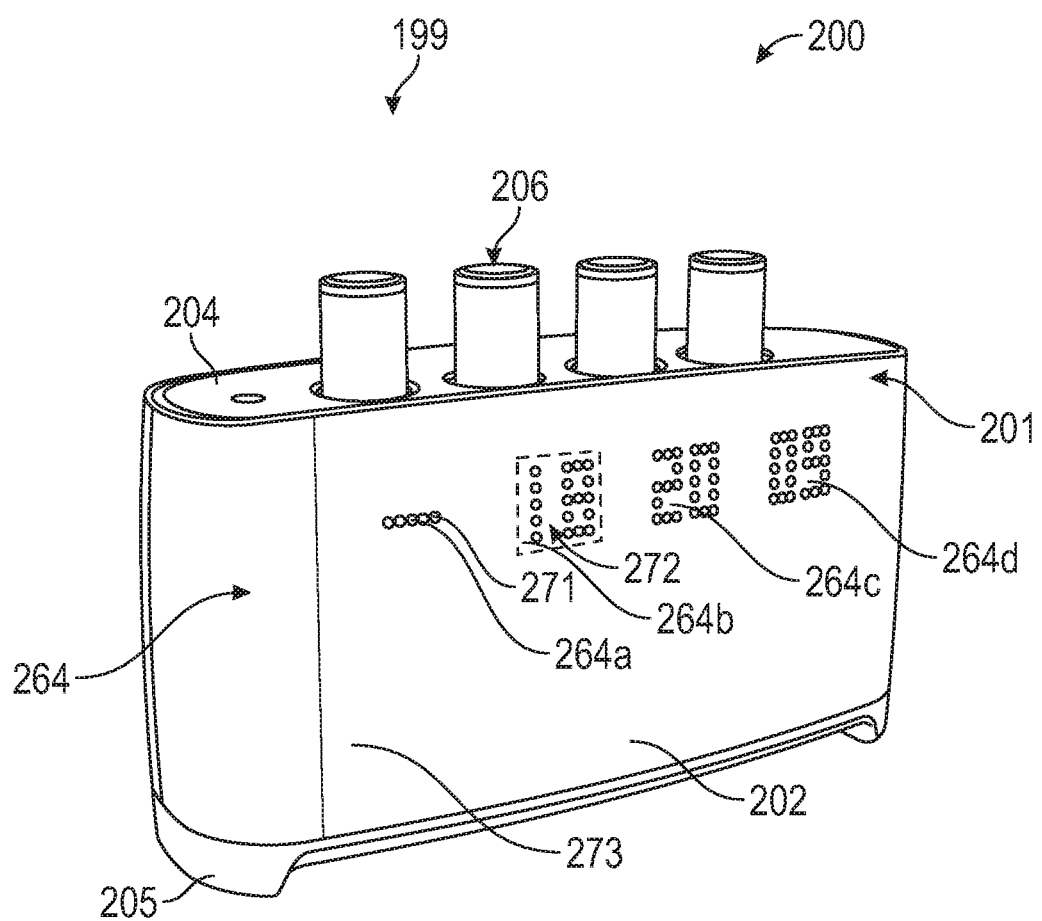
FIG. 7 illustrates a system including sterilization indicators and another embodiment of reading apparatus with a display, according to various embodiments.

The printed circuit board 116 can also have a second side 116B. The second side 116B can be outward facing toward a wall of the housing 101. The printed circuit board 116 can have a second printed circuit board mounted thereon (not shown) to support a display. The display faces outward toward a user as shown in FIGS. 7 and 8.

Figure 3:
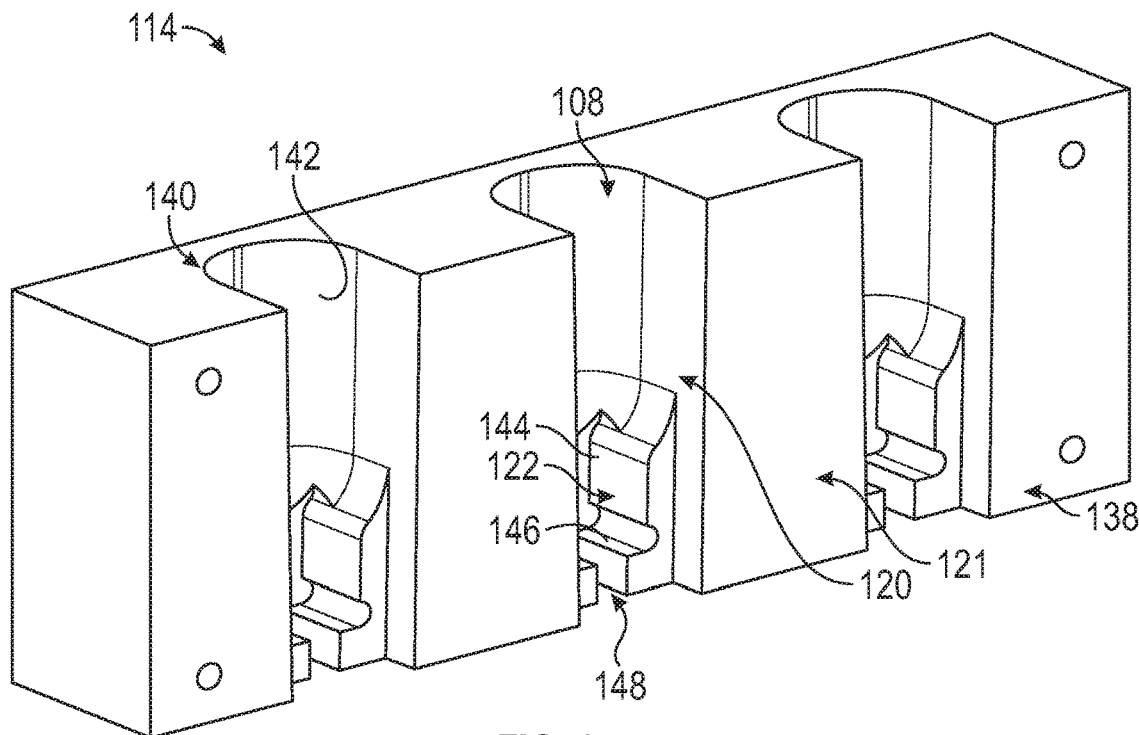
FIG. 3 illustrates a heater block useful in the reading apparatus, according to various embodiments.

FIG. 3 illustrates a more detailed view of the heater block 114. The heater block 114 can have a first surface 138. The first surface 138 can have one or more depressed sections dimensioned to fit a sterilization indicator. The heater block 114 can mate with the spacing device 117 to form the well 108. The heater block 114 can also include baffles 121 formed therein to prevent light from migrating from one well to an adjacent well.

The heater block 114 can include portions that define a first chamber 120, a second chamber 122. For example, the heater block 114 can include a bottom catch 146 in the second chamber 122 for engaging with the spores 107 of the sterilization indicator 106. The heater block 114 can also have a side wall 144 formed therein for engaging with the side of the sterilization indicator 106. A gap 148 can be formed between the bottom catches 146 of the well 108. The gap 148 can allow light into the second chamber 122 (e.g., as part of the sterilization indicator 106 activation detection circuit). The heater block 114 can also include a top portion 104 with curved indentations formed therein (corresponding to 3 wells as shown). The top portion 104 can be configured to catch the cap or another portion of the sterilization indicator 106. The 114 can also include a second well 140 with an first (upper) chamber 142 formed therein.

Figure 4:
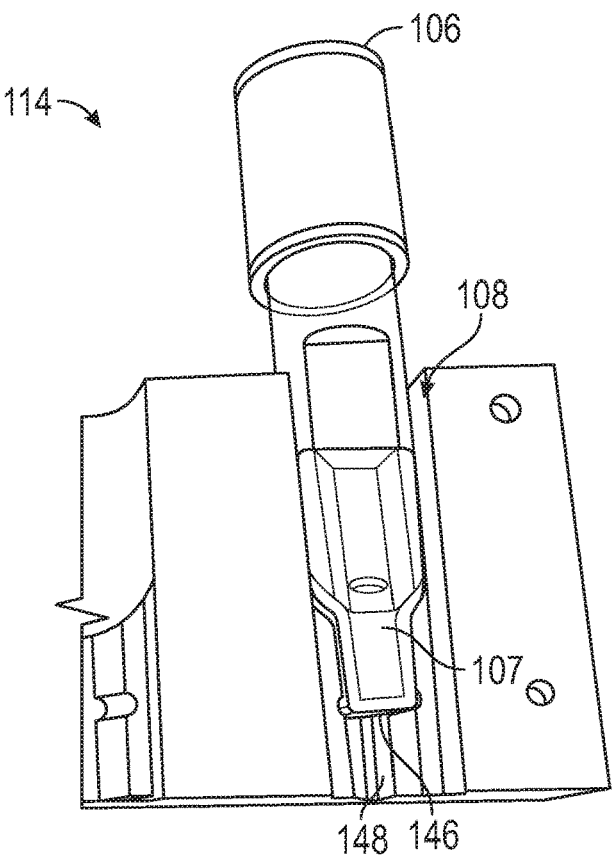
FIG. 4 illustrates a heater block with a sterilization indicator seated therein, according to various embodiments.

FIG. 4 illustrates an example of a sterilization indicator 106 nestled into the heater block 114 with the bottom catch 146 supporting the sterilization indicator 106. A gap 148 can exist in the bottom catch 146 such that light is able to be transmitted into the sterilization indicator 106 by way of the gap 148. The gap 148 is shown at the bottom of the heater block 114, however the gap 148 can also be located on a carved out portion of the baffle (e.g., 121) of the sterilization indicator 106.

Figure 5:
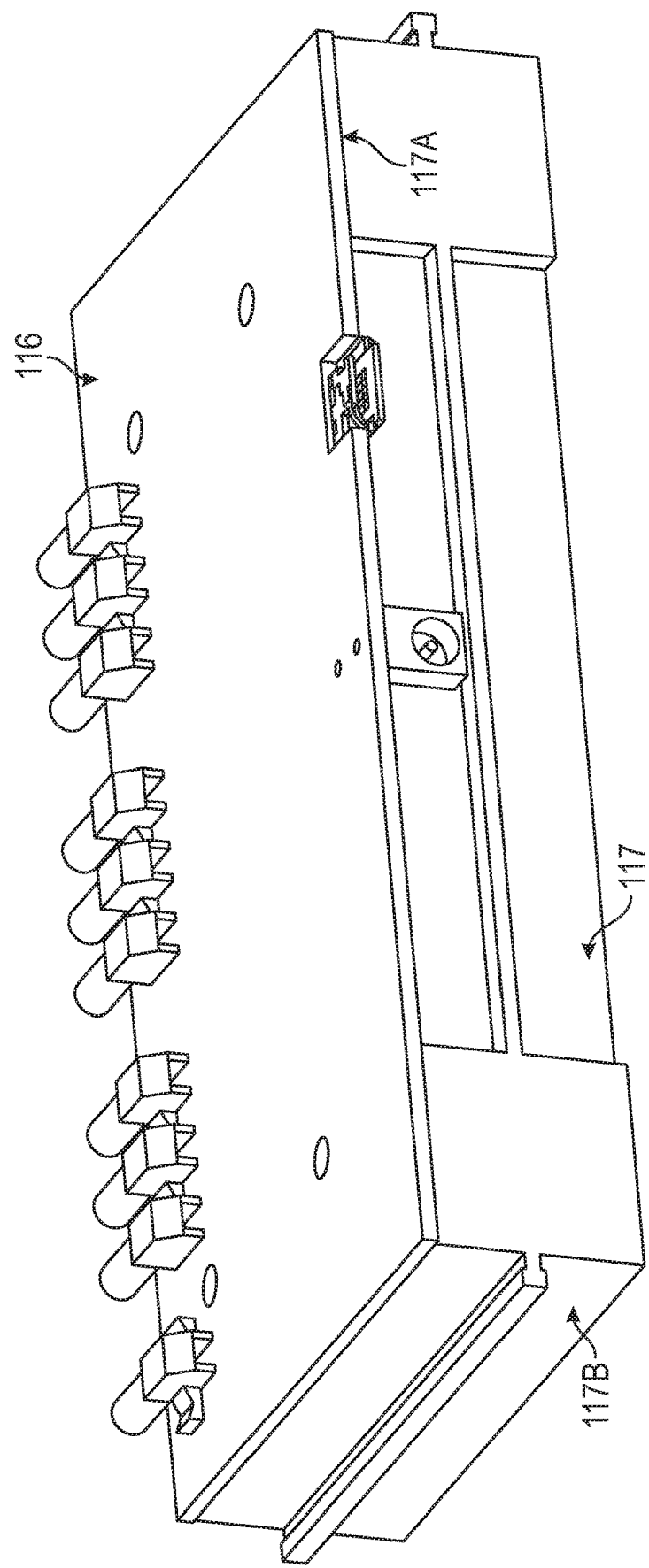
FIG. 5 illustrates the printed circuit board of FIG. 2A-2B attached to a spacing device, according to various embodiments.

FIG. 5 shows the spacing device 117 coupled to the printed circuit board 116. The spacing device 117 has a first side 117A and a second side 117B. First side 117A contacts and is attached to the printed circuit board 116. Second side 117B contacts the heater block 114.

Figure 6A:
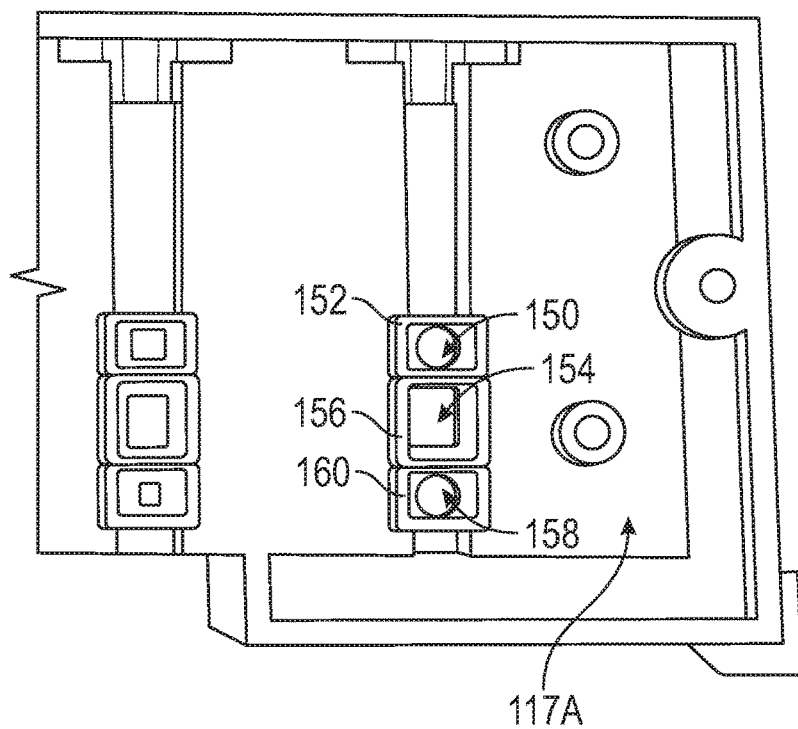
FIGS. 6A-6B illustrate a spacing device useful in the reading apparatus, according to various embodiments.
Figure 6B:
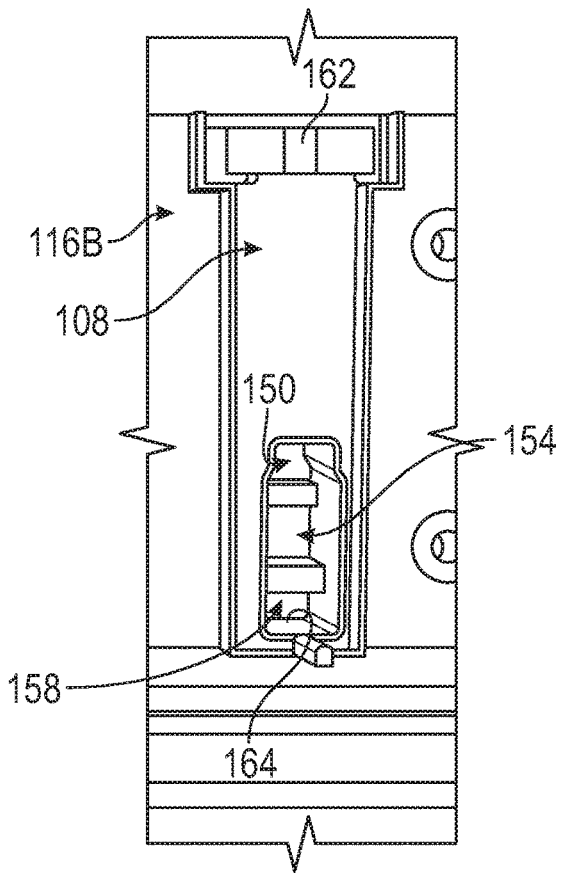

FIGS. 6A-B illustrates a more detailed view of the spacing device 117. The spacing device 117 can have at least one portion that does not interfere with the optical transmission of light from a source. In at least one embodiment, the spacing device 117 can include an air gap, hole, aperture, transparent portion, or combinations thereof in front of multiple LED and color sensors on the printed circuit board. For example, the spacing device 117 can have multiple apertures, 150, 154, 158. In at least one embodiment, light can pass through the aperture 150 to the sterilization indicator 106, and then light can pass through the aperture 154 to color sensor.

The first aperture 150 can focus light onto the sterilization indicator 106. The first aperture 150 can have side walls 152 to direct light toward the well 108. With respect to positioning, the first aperture 150 be aligned with the excitation source. The second aperture 154 can also have a side wall 156 to direct or focus light onto the color sensor. The second aperture 154 can also have one or more features to allow the second aperture to hold an optional filter (e.g., a long pass filter). In addition, the second aperture 154 can have a greater perimeter closer to the sterilization indicator 106 and tapering to a smaller perimeter closer to the color sensor 126 such that light is directed into the color sensor from a larger surface area. The third aperture 158 can also have a side wall 160 to block ambient light. The side wall 160 can focus light onto the sterilization indicator.

In at least one embodiment, the spacing device 117 can include a shelf 162 to further support sterilization indicator 106. The spacing device 117 can also have a sloping wall 164 to focus reflected light onto the color sensor and to ensures spread of the provided light onto a larger surface area of the sterilization indicator 106.

FIG. 7 illustrates a system 199 including an electronic device (also referred to as a reading apparatus) 200 configured to display properties of the indicator 206, such as time remaining on a fluorescence or incubation cycle, and the results. The reading apparatus 200 can have components similar to the reading apparatus 100 with similarly numbered components. The reading apparatus 200 is shown with 4 wells, each well is capable of analyzing the sterilization indicator 206. In at least one embodiment, each well having a separate excitation source, color sensor, and display.

The housing 201 can house electronic components of the reading apparatus 200 and can also house a portion of the sterilization indicator 206. The housing 201 can have a top portion 204, a major side portion 202 (having a curved major side surface or curved major surface and an inside major surface, described herein), and a bottom portion 205. The housing 201 can be formed of a metallic or polymeric material, such as polycarbonate, polyurethane, or polyester. The housing 201 can be opaque such that ambient light does not interfere with the color sensor. For example, the housing 201 can have an average opacity of at least 95 percent, 96 percent, 97 percent, 98 percent, 99 percent, 99.5 percent, or 99.9 percent. An aspect of the present disclosure is that the housing 201, particularly the major side portion 202, is continuous along the curved major surface. For example, no depressed sections on the surface where grime or bacteria can collect. The curved major surface can be curved such that there are no flat faces (e.g., in the x or y dimensions).

The reading apparatus 200 can have a display 264. The display 264 visually communicates information to a user, e.g., minutes remaining, sterilization indicator pass/fail, or combinations thereof for each well. As mentioned earlier, each well can have its own display independent from another display for another well. As shown, there are a plurality of displays with one display per well. For example, displays 264a and 264d can be outer arrays of display elements corresponding to the outer wells of the reading apparatus 200 (closest to the edge of the housing 202A). Displays 264b and 264c can be inner arrays of display elements corresponding to the inner wells of the reading apparatus 200. In at least one embodiment, the thickness of the major side portion 202A can be greater proximate the inner wells than in the outer wells. The displays 264b and 264c can be brighter than displays 264a and 264d.

An aspect of the present disclosure is that the display 264 illuminates through the housing 201, preferably through the major side portion. The major portion is aligned along the x-dimension of the reading apparatus 200. The major side portion 202 can have varying levels of opacity. For example, a display area (e.g., 271, 272) of the major side portion 202 can be have a lower thickness than section 273 (which is outside of display areas 271 and 272).

In at least one embodiment, each display 264a can have a display area 271. The display area is a region of the curved major surface whereby a display element (or an array of display elements) is projected. In at least one embodiment, the opacity of the display area is no greater than 95 percent, no greater than 93 percent, no greater than 90 percent, or no greater than 85 percent. In at least one embodiment, the opacity of the display area is at least 50 percent, at least 60 percent, at least 70 percent, or at least 80 percent. The display area (e.g., 271) can be on the curved major surface. In at least one embodiment, the display area includes one or more depressed sections 274 that forms a thinner portion relative to the major portion 202A. The array of display elements can align with the depressed sections 274. As used herein, array can refer to an ordered arrangement of display elements. In at least one embodiment, array can mean horizontal rows and vertical columns in an orderly arrangement.

In at least one embodiment, the display 264 is backlit sufficient to provide light through the major side portion 202. The display 264 can have a plurality of display elements, e.g., electronic devices that allow functioning of the display as a whole. In one example, the display element 270 is an LED such that the display 264a can be an array of LEDs. Within the housing 202 can be one or more sections that correspond to placement of the display element such that the display element is aligned with a depressed section. In at least one embodiment, the display 264a can be an eight-segment display, nine-segment display, fourteen-segment display, sixteen-segment display, a dot matrix display, an array of LEDs, or combinations thereof. The display 264a can be individual for each well 108 and is capable of displaying alphanumeric characters such as numbers, positive symbol, negative symbol, and combinations thereof.

The display 264 is of sufficient size and brightness such that the displayed object is visible from at least 10 ft away, at least 20 ft away, or at least 30 ft away, under typical office lighting, for an average human. For example, display area 272 (e.g., a 2 digit number for the well) can be at least 1% of the total surface area of the major side portion 202 (e.g., the mostly flat major face portion excluding the curves). In another example, the total display size (e.g., the combined display area for all wells) can be at least 1 percent, at least 5 percent, or at least 10 percent of the total surface area of the major side portion 202. In at least one embodiment, the section 273 can be at least 4 cm$^2$, at least 6 cm$^2$, or at least 8 cm$^2$.

The display 264 can have an internal output value within the housing (or uncovered) 201 of at least 1 lumen, at least 2 lumens, at least 3 lumens, at least 4 lumens, or at least 5 lumens. In at least one embodiment, the display can have an internal output value no greater than 100 lumens, no greater than 50 lumens, or no greater than 10 lumens. Outside of the housing 201, the external output value through the housing 201 can be at least 0.15 lumens, at least 0.30 lumens, at least 0.45 lumens, or at least 1 lumen. In at least one embodiment, the internal output value can be at least 10 times, at least 15 times, or at least 20 times the external output value.

FIG. 8A-8D illustrates a system including the reading apparatus 200 and a sterilization indicator. The reading apparatus 200 can include housing 201 having a major side portion 202 which includes a first portion 202A and a second portion 202B joined together. As described herein, major side portion 202 can have a curved major surface 202A1 corresponding to the outward facing surface. The housing 201 also includes a top portion 204 and a bottom portion 205. In at least one embodiment, the top portion 204, bottom portion 205, and first portion 202A and the second portion 202B are separate components.

Figure 8D:
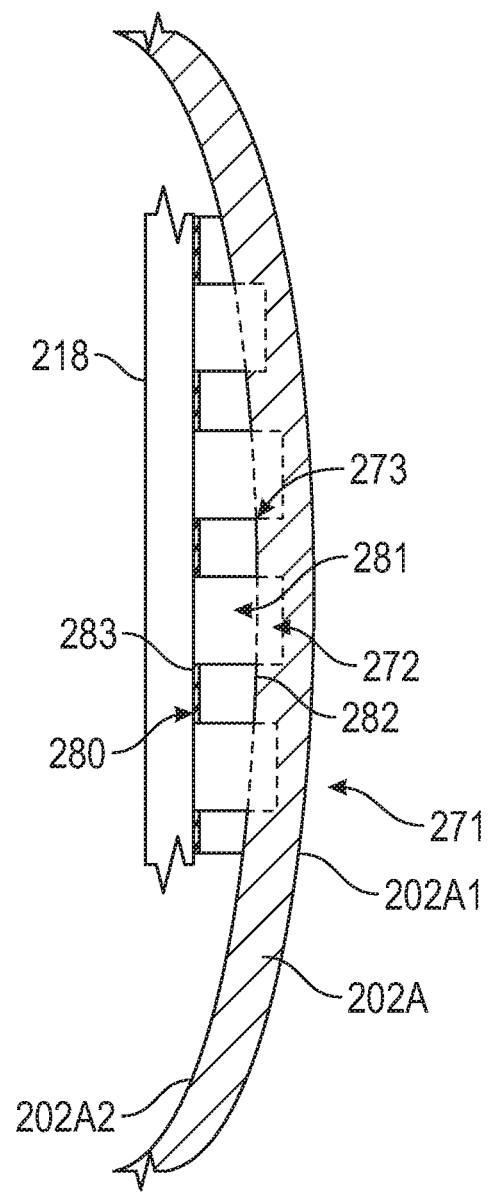
FIG. 8D illustrates a cross-sectional view of the major side portion of FIG. 8B along lines 8D-8D, according to various embodiments.

In at least one embodiment, the major side surface of the major side portion 202 is continuously curved along at least one axis (e.g., a horizontal or vertical axis), meaning that it is rounded without interruption. For example, FIG. 8D illustrates the curved major surface 202A1 in greater detail as curved surface and not a planar surface. Displays that illuminate through a housing typically have a housing having an outer flat or outer planar surface for the display. When light is illuminated from a display element through a curved surface, the resulting image can appear warped to a user. An aspect of the present disclosure is using a gasket 280 that substantially conforms to the housing to ensure adequate resolution of the resulting display.

The reading apparatus 200 also includes a spacing device 217, heater block 214, printed circuit board 216, a second printed circuit board 218 (having one or more display elements disposed thereon), heating element 215. The heating element 215 is coupled to the heater block 214, the heater block 214 is coupled to the spacing device 217. the spacing device 217 is coupled to the first printed circuit board 216, the second printed circuit board 218 is coupled to the first printed circuit board 218. In at least one embodiment, the second printed circuit board 218 is planar and rigid. The plurality of display elements from multiple displays 264 can be surface mounted to the second printed circuit board 218 such that the plurality of display elements are planar. The heating element 215 can also be thermally coupled to the back of the heater block 214 and electrically coupled to the printed circuit board 116. In at least one embodiment, the heating element 215 can be disposed within the front (defined by the wells) of the heater block 214. Thus, the planar plurality of display elements can be projected into curved major surfaces of the reading apparatus 200.

In at least one embodiment, the second printed circuit board 218 can further have a gasket 280 disposed thereon such that light from a display element is shown through apertures 281 and passed through the housing. The gasket 280 can be optional. Each aperture is dimensioned to receive the display element. In at least one embodiment, the aperture 281 can have a tolerance of no greater than 1 mm with respect to the display element. In at least one embodiment, the gasket 280 has a curved surface 282 to conform to the housing 201 and a planar surface 283 to align with the second printed circuit board 218. The gasket 280 not need to molded and could be additive, die cut, stamped, or overmolded onto the housing 201.

The first portion 202A can have a first surface 202A1 and a second surface 202A2. The first surface 202A1 can be outwardly facing and the second surface (inside major surface) 202A2 can face toward the electronic components of the reading apparatus 200. Section 273 can have a thickness dimension 277 that is greater than the thickness dimension 278 which corresponds to display area 272.

The second surface 202A2 can have one or more depressed sections 274. The depressed section 274 can have a depressed dimension 276 that is depressed relative to the second surface 202A2. Each depressed section 274 can align with the display or a display element. A depressed section (e.g. 274) can also include a sidewall 286 mostly perpendicular to the curved major surface 202A1 or inside major surface 202A2. The depression side wall 286 can abut the depression bottom surface 284. The depression bottom surface 284 is preferably flat and oriented with the curved major surface 202A1 or inside major surface 202A2. The junction between the depression side wall 286 and the depression bottom surface 284 can be mostly perpendicular. For example, the corner radius 285 between the depression side wall 286 and the depression bottom surface 284 can be no greater than 0.5 mm, no greater than 0.25 mm. It was advantageously found that a smaller corner radius 285 can lead to better resolution of the resulting display.

As shown, the housing includes a plurality of depressed sections to correspond to a plurality of display elements (e.g., LEDs). Although not shown, the plurality of depressed sections can be arranged an a horizontal alignment (rows) and vertical alignment (columns). A depressed section can have a pitch within a display area where a depressed section is located at least 2.5 mm horizontally from a horizontally adjacent depressed section, and at least 3.5 mm vertically from a vertically adjacent depressed section. In at least one embodiment, the thickness dimension 278 is at least 0.1 or 0.5 mm and the thickness dimension 277 is at least 1 mm, or 2 mm.

Figure 9:
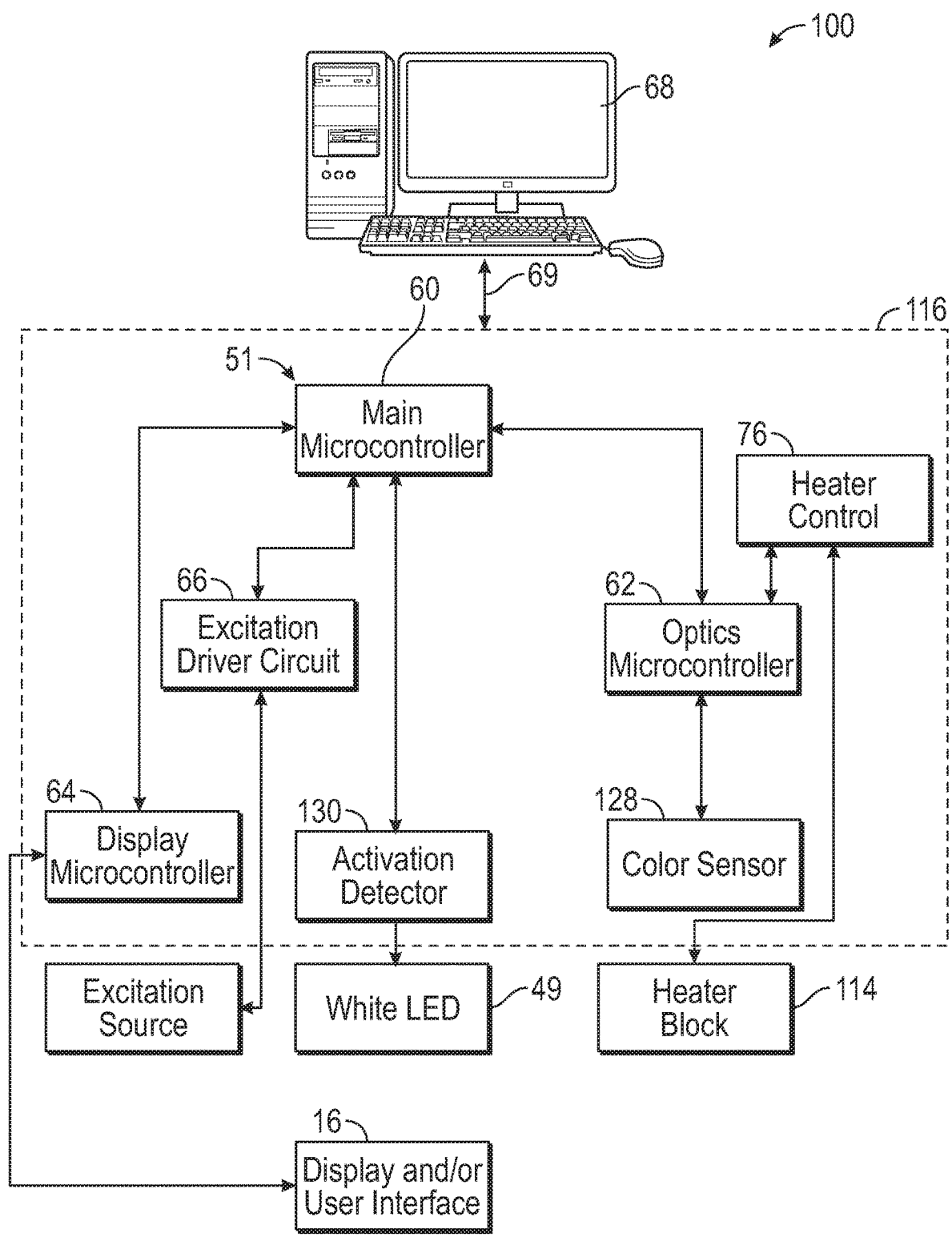
FIG. 9 illustrates a block diagram of the controller circuit, according to various embodiments.

FIG. 9 illustrates the reading apparatus 100 or reading apparatus 200 which can synchronously process multiple sterilization indicators without user intervention. In addition, the reading apparatus 100 can combine the incubation site and reader site to a common location. Fluorescence values can be read for each well independently. Each well of the reading apparatus can include a corresponding display area (e.g., an LCD display) on the display 16 of the reading apparatus to display sterilization indicator processing results to a user, and optionally, well number, time remaining, temperature, and/or other general information.

The printed circuit board 116 can include three microcontrollers: a main microcontroller 60, an optics microcontroller 62, and a display microcontroller 64. The three microcontrollers 60, 62 and 64 can collectively be referred to as the "controller circuit" 51 of the reading apparatus 100. The controller circuit 51 can include one or more processors that are communicatively coupled to a memory.

The controller circuit 51 can be configured to control the various processing and executing portions of the reading apparatus 100. Generally, the controller circuit 51 (or microcontrollers 60, 62 and 64) can be a suitable electronic device, such as, for example, a programmable logic controller ("PLC"), a microprocessor, a personal computer ("PC"), another industrial/personal computing device, or combinations thereof. As such, the controller circuit 51 may include both hardware and software components, and is meant to broadly encompass the combination of such components. The breakdown of the controller circuit 51 is shown by way of example only.

The main microcontroller 60 can control an excitation driver circuit 66 for driving excitation sources, such as LEDs. The excitation driver circuit 66 can include a 3 or 4-channel constant current driver in which each channel is controlled individually, and can connect to an array of LEDs (e.g., UV LEDs) on the printed circuit board. Each channel of the 3 or 4-channel current driver can be calibrated/normalized to accommodate variations from channel to channel. The main microcontroller 60 can also detect insertion and/or activation of sterilization indicators by controlling sterilization indicator activation detection circuits 130, in conjunction with the white LEDs 49. The sterilization indicator activation detection circuits 130 each include the color sensor that can allow the main microcontroller 60 to monitor the insertion or removal of sterilization indicators relative to a corresponding well, as well as the detection of activation of the sterilization indicators. The main microcontroller 60 can also obtain emission readouts from the optics microcontroller 62; control the display microcontroller 64, and communicate with a host computer 68 via an Ethernet, or wireless communication 69.

The optics microcontroller 62 can provide control of the color sensor 128. The optics microcontroller 62 can also provide control of the temperature of the heater block 114 via a heater control 76. The heater control 76 can include a closed-loop system that monitors the temperature of the heater block 114 and turns the heater block 114 on and off accordingly.

Furthermore, in some embodiments, the reading apparatus 100 (e.g., the optics microcontroller 62) can be adapted to minimize the effects of temperature variation on various electronic components of the reading apparatus 100, such as the color sensor 128 (e.g., for fluorescence detection). That is, in some embodiments, temperature variations of various optical components can be determined and eliminated. In such embodiments, the temperature of various optical components and/or ambient temperature can be monitored, a correction factor can be determined, and the correction factor can be used to normalize the output from such optical components. Such adjustments can minimize fluctuations in output that may be the result of temperature variation, and can improve the accuracy of the assay results of the reading apparatus 100 (e.g., regarding sterilization efficacy).

The display microcontroller 64 can receive information from the main microcontroller 60, can generate character sets, and can display information and/or capture information from the display and/or user interface 16. The display 16 can display status information and can provide error codes to a user.

Figure 10:
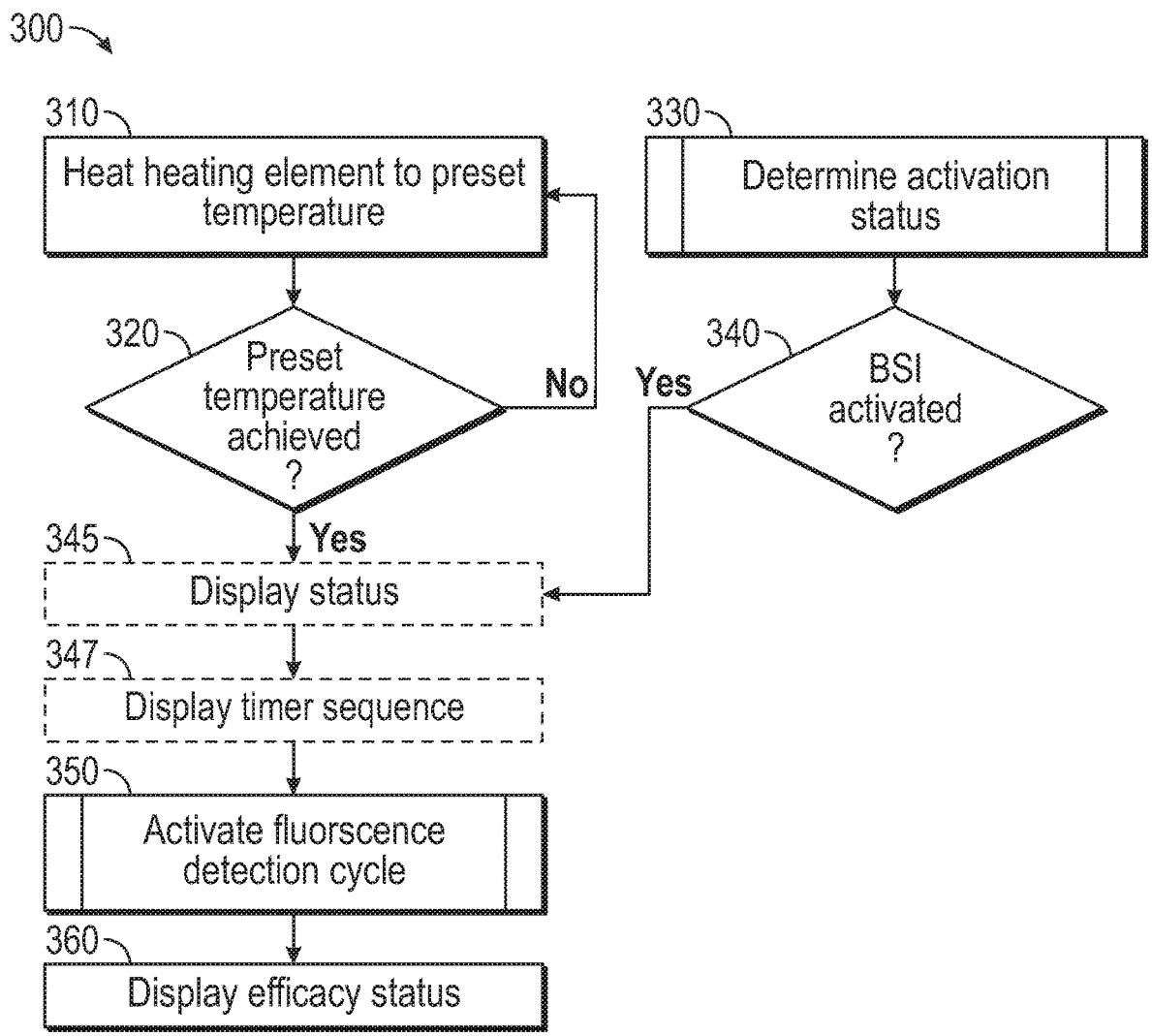
FIG. 10 illustrates a flowchart of a method of operation of the reading apparatus, according to various embodiments.

FIG. 10 illustrates a method 300 of operating the reading apparatus described herein. The method 300 can begin with block 310.

In block 310, the heater control 76 can heat heating element to a preset temperature, i.e., activate the heating element and heat the heating element or heater block from a first temperature to a second, preset temperature. The heat from the heating element can be distributed over the heater block to provide even temperature of the sterilization indicator. The temperature sensor can sense the temperature of the heater block, heating element, medium, or combinations thereof. In at least one embodiment, the heating element can heat medium directly. The preset temperature can be different for each well depending on the type of sterilization indicator or user preferences. For example, a first well can be heated to 60 degrees Celsius and the second well can be heated to 54 degrees Celsius.

In at least one embodiment, block 310 can also be referred to as an incubation cycle and can also occur in response to the sterilization indicator being present and activated (meaning that nutrient medium is present). The heater control can also be configured achieve the second temperature within 20 minutes of the reading apparatus 200 being turned on from room temperature (i.e., Standard Temperature and Pressure). In at least one embodiment, activating the fluorescence detection cycle described in block 350 occurs in response to the second (preset) temperature being achieved.

In block 320, the heater control 76 can determine whether the preset temperature is achieved. The preset temperature can be dependent on the sterilization indicator type. If the preset temperature is reached, then the method 300 can continue to block 350.

In block 330, the activation detection circuit can determine activation status. In at least one embodiment, the activation detection circuit can detect the presence of medium inside of the sterilization indicator. In addition, the medium color can allow the heater control to determine the preset temperature. For example, the presence of a green color can cause the heater control to preset the preset temperature to 54 degrees Celsius. In at least one embodiment, the activation status can be determined continuously over the entire period of a fluorescence detection cycle (e.g., block 350) to verify that there is an activated sterilization indicator present in the well. If, after the sterilization indicator is activated, the sterilization indicator is later removed from the well during a fluorescence detection cycle, then an error can be triggered and the fluorescence detection cycle stopped. Alternatively, the if the sterilization indicator is layer removed during a fluorescence detection cycle after being activated, then an automatic failure indication can be triggered to reset the cycle. In block 340, if the sterilization indicator is activated, then the method 300 can continue to block 350.

In at least one embodiment, the method 300 can continue to block 345 in response to either block 340 or 320, or both being affirmative. For example, the controller circuit can cause the display microcontroller to display a status of the preset temperature being reached. In at least one embodiment, the status can be a color change of the display to indicate that the reading apparatus is ready to receive the sterilization indicator. This can happen before or after an sterilization indicator is inserted into the well and the activation status of the sterilization indicator is determined in block 330.

In block 347, the controller circuit can, via the display microcontroller, cause the display to display a timer sequence. The timer sequence can indicate the amount of time for the reading apparatus to yield a positive or negative result of the sterilization indicator. For example, the timer sequence can be activated based on an indication that the sterilization indicator has been activated in block 340. Once activated, then the controller circuit can start a predetermined timer sequence that approximates the time until a sterilization efficacy determination is achieved. In at least one embodiment, removal of the sterilization indicator from the well can result in a pause of the timer sequence, whereby reinsertion of the sterilization indicator can resume the timer sequence. In at least one embodiment, the removal of the sterilization indicator from the well can result in a non-efficacious determination for safety, and/or an error indication.

In block 350, the controller circuit can activate a fluorescence detection cycle to determine the sterilization efficacy of the sterilizer based on the sterilization indicator. For example, the excitation driver circuit can activate the fluorescence detection cycle where the excitation source is activated and fluorescence received by the color sensor. In at least one embodiment, block 350 can occur based on both the sterilization indicator being activated and the preset temperature being reached. In at least one embodiment, the incubation cycle and the fluorescence detection cycle are not mutually exclusive, thus the fluorescence detection cycle can occur at least partially concurrently with the incubation cycle. The timer sequence can be based off of the incubation cycle, fluorescence detection cycle, or combinations thereof.

Once block 350 has commenced, the display microcontroller can concurrently display a time remaining of the fluorescence detection cycle so that the user can be alerted. In at least one embodiment, the time remaining can be the output of the timer sequence where increments of time (e.g., hours, minutes, seconds) are decremented until zero. Block 350 is described further herein.

In at least one embodiment, the timer sequence of block 347 can also be determined based on a prediction of the fluorescence detection cycle. For example, if the fluorescence indicates poor growth of the spores, then the controller circuit can shorten the timer sequence based on the prediction. The prediction can be based on feedback of low fluorescence from the sterilization indicator.

In block 360, after the sterilization efficacy is determined, the controller circuit via the display microcontroller can further display the sterilization efficacy on the display. The results of the sterilization efficacy can be either positive, negative or error. The results can be displayed individually on each well.

Figure 11:
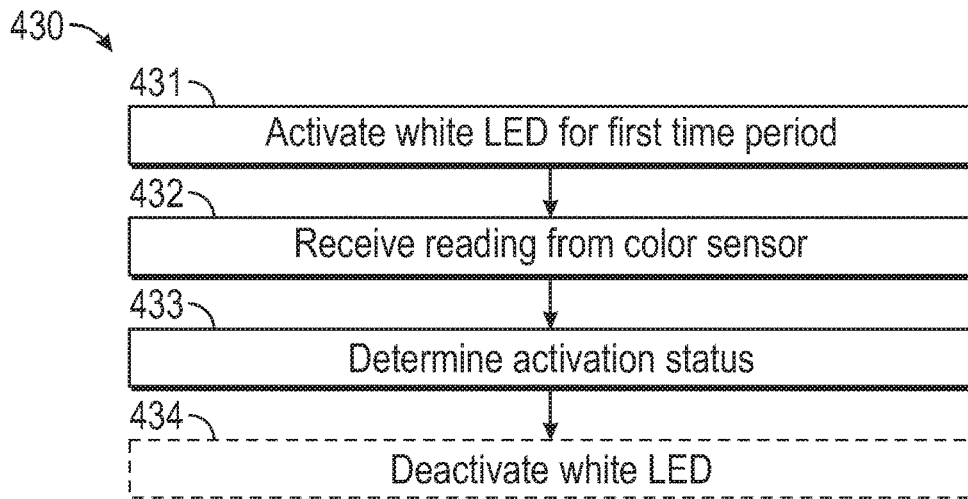
FIG. 11 illustrates a flowchart of a method of determining activation status of the sterilization indicator, according to various embodiments.

FIG. 11 illustrates a method 430 of determining activation status of a sterilization indicator. The method 430 can be an embodiment of block 330 of FIG. 10. In at least one embodiment, method 430 can relate to a visual detection of the medium by a color sensor.

The method 430 can begin at block 431. In block 431, the detection circuit can activate the white LED for a first time period. For example, a white LED can determine the color of a chamber in the sterilization indicator. The presence or absence of a color can correspond to a color of the medium.

In block 432, the detection circuit can receive a first reading from the color sensor corresponding to a first plurality of color channels. The color sensor can determine the color channels based on the reflectance of the white light on the chamber of the sterilization indicator. For example, the plurality of color channels can correspond to a color other than white light if a colored medium is present or can correspond to white light if there is no medium present.

In block 433, the detection circuit can determine activation status of the sterilization indicator based on the first plurality of color channels. In response, the controller circuit can optionally deactivate the white LED if the sterilization indicator is activated in block 434.

In at least one embodiment, if the sterilization indicator is activated, then the white LED can be periodically activated and the color analyzed (i.e., blocks 431-433 can be ongoing until the end of the fluorescence detection cycle). In at least one embodiment, the white LED can be always activated and the plurality of color channels monitored periodically to ensure that the sterilization indicator is activated. Various functions can also be triggered based on results from block 433. For example, the controller circuit can be configured to display a time remaining on an incubation cycle or fluorescence detection cycle of the sterilization indicator. If block 433 is negative after a positive reading with a particular time period, then a timer sequence can be reset if the sterilization indicator is removed.

Figure 12:
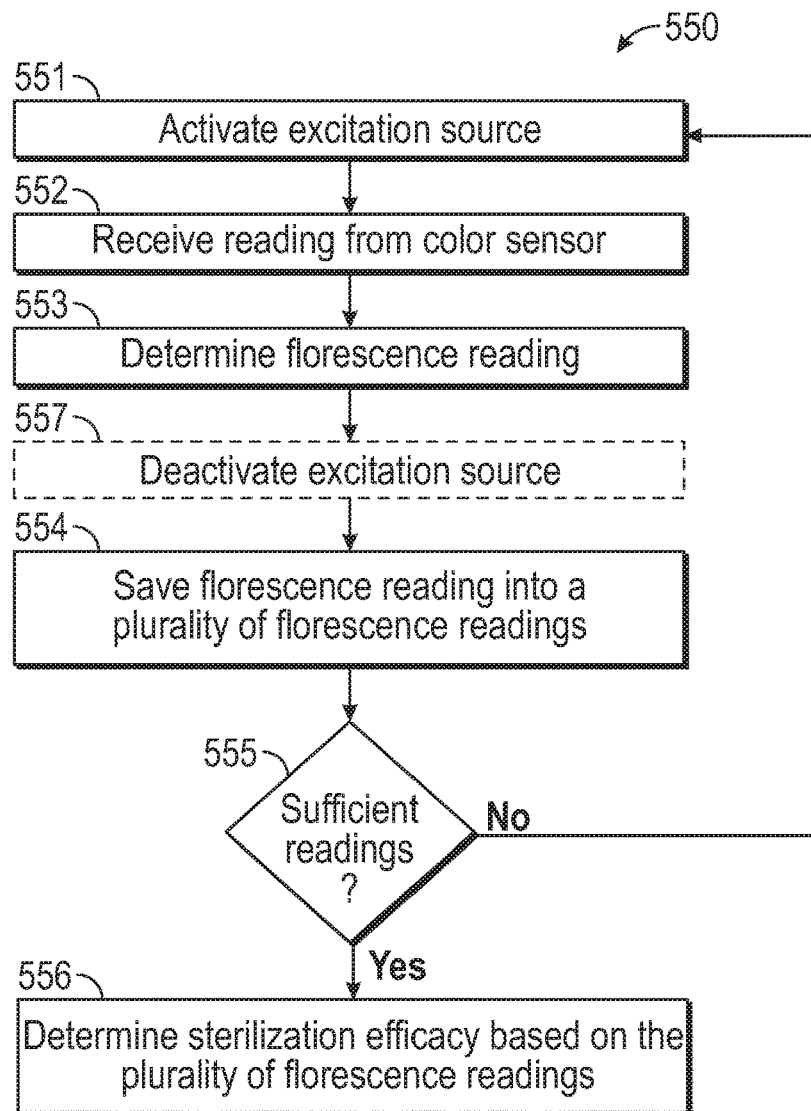
FIG. 12 illustrates a flowchart of a method of determining sterilization efficacy of the sterilization indicator, according to various embodiments.

FIG. 12 illustrates a method 550 of activating a fluorescence detection cycle to determine sterilization efficacy. The method 550 can correspond to block 350 from FIG. 9. The method 550 can involve determining sterilization efficacy a variety of methods, such as area under the curve, root-mean-squared, thresholding, etc.

In block 551, the excitation driver circuit can activate the excitation source for a second time period. In at least one embodiment, the second time period for activating the excitation source does not overlap with the first time period for activated the white LED in block 431. In addition, the first time period can have a first duration that is less than a second duration of the second time period such that the white LED is not activated for as long as the excitation source. For example, the first time period can have a first duration of no greater than 1 second, and the second time period can have a second duration of greater than 1 second.

In other embodiments, the second time period can overlap with the first time period such that both the excitation source and the white LED are activated at the same time.

In block 552, the controller circuit can receive a second reading from the color sensor corresponding to a second plurality of color channels. In at least one embodiment, the second plurality of color channels can be different than the first plurality of color channels such that the color channels do not have the same signatures. The controller circuit can receive the second reading at the same time as in block 432 and perform the analysis concurrently or in parallel. In block 553, the controller circuit can determine a fluorescence reading from the second reading.

In block 557, the controller circuit can deactivate the excitation source based on the fluorescence reading being determinable. Determinable can mean the fluorescence is able to be determined from the color sensor. If the color sensor provides color channels not corresponding to an appropriate fluorescence spectrum (i.e., wrong wavelengths), then the fluorescence is not determinable. Block 557 can be optional.

In block 554, the controller circuit can optionally save the florescence reading into memory. The fluorescence reading in the memory can be optionally analyzed at a later time or a trend can be ascertained. For example, in block 555, the controller circuit can determine if there are a sufficient number of fluorescence readings to ascertain a trend.

In block 556, the controller circuit can determine the sterilization efficacy based on analyzing the plurality of fluorescence readings. For example, if the plurality of fluorescence readings indicates an increasing fluorescence readings relative to a level of biological growth, then the faster rate of biological growth likely indicates that the sterilization process was not effective. If the plurality of fluorescence readings is not increasing or increasing at a slower rate, then the controller circuit can conclude that a sterilization process was effective. One or more operations can be performed by the controller circuit in response to a non-effective or an effective sterilization cycle. For example, a display can indicate that the cycle is complete and display whether the sterilization indicator indicates an effective sterilization cycle.

In this application:

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

Terms such as "a", "an" and "the" are not intended to refer to only a singular entity, but include the general class of which a specific example may be used for illustration. The terms "a", "an", and "the" are used interchangeably with the term "at least one".

The phrase "comprises at least one of" followed by a list refers to comprising any one of the items in the list and any combination of two or more items in the list. The phrase "at least one of" followed by a list refers to any one of the items in the list or any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

All numerical ranges are inclusive of their endpoints and nonintegral values between the endpoints unless otherwise stated (e.g., 1 to 5 includes 1, 1.5, 2, 2.75, 3, 3.80, 4, 5, etc.).

List of Illustrative Embodiments

1. A sterilization indicator reading apparatus, comprising:
    a housing comprising a top portion, a bottom portion, and a major side portion;
    a well formed from a portion of the housing, accessible from the top portion, and oriented along a well axis from the top portion to the bottom portion, the well dimensioned to receive at least a portion of a sterilization indicator having spores and a substance fluorescently responsive to spore concentration and the spores are responsive to an environmental condition in a sterilizer;
    a heating element thermally coupled to a portion of the well;
    an excitation source to excite the substance in the sterilization indicator;
    a sterilization indicator activation circuit for detecting activation of the sterilization indicator, wherein the excitation source is positioned such that light from the excitation source is directed into the well,
    a color sensor positioned adjacent the well, wherein the color sensor is positioned to receive light from the sterilization indicator;
    a controller circuit comprising:
        a processor,
        a memory communicatively coupled to the processor, wherein the heating element, excitation source, the color sensor, and sterilization indicator activation circuit are communicatively coupled to the processor.
2. The sterilization indicator reading apparatus of any of embodiments 1, further comprising: a first printed circuit board having the excitation source, color sensor, and controller circuit disposed thereon, wherein the first printed circuit board forms a first plane that is oriented parallel with the well axis.
3. The sterilization indicator reading apparatus of embodiment 2, wherein the first printed circuit board has a plane that is substantially parallel to a plane of the major side portion.
4. The sterilization indicator reading apparatus of embodiment 2, wherein the sterilization indicator has a vertical axis defined by a cap and a tip, and the vertical axis is parallel to a plane formed by the first printed circuit board.
5. The sterilization indicator reading apparatus of embodiment 2, further comprising a plurality of wells including the first well, wherein the first printed circuit board is continuous such that the excitation source, a white LED, and color sensor of the first well is on the same printed circuit board as an excitation source, a white LED, and color sensor of a second well.
6. The sterilization indicator reading apparatus of embodiment 2, further comprising a second printed circuit board having a display thereon, the second printed circuit board is parallel to the first printed circuit board.
7. The sterilization indicator reading apparatus of any of embodiments 1 to 6, wherein the display comprises a plurality of display elements.
8. The sterilization indicator reading apparatus of embodiment 7, wherein the display element is a single LED.
9. The sterilization indicator reading apparatus of embodiment 8, further comprising: a plurality of LEDs disposed proximate the first printed circuit board, the plurality of LEDs arranged to display a number corresponding to a time.
10. The sterilization indicator reading apparatus of embodiment 8, wherein the plurality of LEDs are abutting a portion of the housing such that the plurality of LEDs are visible through the housing.
11. The sterilization indicator reading apparatus of any of embodiments 1 to 10, wherein the major side portion has a first side facing outward and a second side facing toward the color sensor, the major side portion having depressed section formed thereon the second side.
12. The sterilization indicator reading apparatus of embodiment 11, wherein the first section has a first thickness and the second section has a second thickness, the first thickness is greater than the second thickness.
13. The sterilization indicator reading apparatus of any of embodiments 1 to 12, further comprising a one-way reflective uniform coating disposed on the housing such that light is impeded into the housing.
14. The sterilization indicator reading apparatus of any of embodiments 1 to 13, wherein the memory comprises instructions that when executed by the processor, causes the processor to determine whether the sterilization indicator is activated.
15. The sterilization indicator reading apparatus of embodiment 14, wherein the sterilization indicator activation circuit detects a liquid medium color of the sterilization indicator.
16. The sterilization indicator reading apparatus of embodiment 15, wherein the color sensor is positioned to detect activation status of the sterilization indicator.
17. The sterilization indicator reading apparatus of embodiment 15, wherein the sterilization indicator activation circuit comprises a white LED positioned such that light from the white LED is directed into the well and reflected light that originates from the white LED is received by the color sensor.
18. The sterilization indicator reading apparatus of embodiment 14, wherein, to determine whether the sterilization indicator is activated, the memory comprises instructions that when executed by the processor causes the processor to:
activate the white LED for a first time period,
receive a first reading from the color sensor corresponding to a first plurality of color channels, and
determine presence of the sterilization indicator based on the first plurality of color channels.
19. The sterilization indicator reading apparatus of embodiment 18, wherein the memory comprises instructions that when executed by the processor, causes the processor to:
determine activation status of the sterilization indicator based on the first plurality of color channels.
20. The sterilization indicator reading apparatus of embodiment 19, wherein the memory comprises instructions that when executed by the processor, causes the processor to: deactivate the white LED in response to the sterilization indicator being activated.
21. The sterilization indicator reading apparatus of embodiment 19, wherein the processor determines the activation status of the sterilization indicator based on the first plurality of color channels corresponding to a purple color.
22. The sterilization indicator reading apparatus of any of embodiments 1 to 21, wherein the sterilization indicator is a self-contained biological sterilization indicator.
23. The sterilization indicator reading apparatus of embodiment 22,
the sterilization indicator comprising an indicator housing including:
a first portion, and
a second portion adapted to be coupled to the first portion, the second portion being movable with respect to the first portion, when coupled to the first portion between a first position and a second position; and
a container containing a medium and being dimensioned to be positioned in the indicator housing, at least a portion of the container being frangible, the container having a first state in which the container is intact when the second portion of the indicator housing is in the first position, and a second state in which the container is fractured when the second portion of the indicator housing is in the second position;
a first indicator chamber within the indicator housing in which the container is positioned when the container is in the first state; and
a second indicator chamber within the indicator housing in which the container and the medium are not positioned when the container is in the first state, and into which the medium moves when the container is in the second state, the second chamber comprising at least one source of biological activity that is not in fluid communication with the medium when the container is in the first state and that is in fluid communication with the medium when the container is in the second state.

24. The sterilization indicator reading apparatus of embodiment 23, wherein the indicator housing includes at least one substantially planar outer wall positioned adjacent the second indicator chamber.

25. The sterilization indicator reading apparatus of embodiment 23, wherein the color sensor is positioned adjacent a region of the well dimensioned to receive at least a portion of the second indicator chamber.

26. The sterilization indicator reading apparatus of embodiment 23, wherein the color sensor is positioned to detect at least one of:
the sterilization indicator being positioned in the well with the medium not being present in the second indicator chamber, and
the sterilization indicator being positioned in the well with the medium being present in the second indicator chamber.

27. The sterilization indicator reading apparatus of embodiment 26, wherein the color sensor is positioned to detect whether the at least one source of biological activity survived a sterilization process.

28. The sterilization indicator reading apparatus of embodiment 26, wherein the color sensor is positioned to detect whether the medium is present in the second indicator chamber.

29. The sterilization indicator reading apparatus of embodiment 23, wherein the sterilization indicator is keyed with respect to the well, such that the sterilization indicator is positioned fully within the well in only one orientation.

30. The sterilization indicator reading apparatus of any of embodiments 1 to 29, further comprising a long pass filter disposed on the color sensor thereon.

31. The sterilization indicator reading apparatus of embodiment 30, wherein the color sensor or long pass filter blocks UV light.

32. The sterilization indicator reading apparatus of embodiment 31, wherein the long pass filter filters light less the 435 nm and allows light having a wavelength more than 435 nm.

33. The sterilization indicator reading apparatus of any of embodiments 1 to 32, further comprising a heating element electrically coupled to the controller circuit.

34. The sterilization indicator reading apparatus of embodiment 33, further comprising a heater block forming a portion of the well, the heating element is thermally coupled to the heater block.

35. The sterilization indicator reading apparatus of embodiment 34, wherein the well comprises a first chamber and a second chamber, wherein the second chamber has a smaller perimeter than the first chamber.

36. The sterilization indicator reading apparatus of embodiment 33, wherein the controller circuit is configured to activate the heating element and heat the heating element or heater block from a first temperature to a second temperature.

37. The sterilization indicator reading apparatus of embodiment 36, wherein one or more indicator LEDs distinct from the display are visible to a user, a first indicator LED indicate that the heating element is activated and a second indicator LED indicates whether a second temperature has been achieved.

38. The sterilization indicator reading apparatus of embodiment 36, wherein the second temperature is achieved within 20 minutes of receiving power.

39. The sterilization indicator reading apparatus of embodiment 37, wherein the second temperature is 60 degrees Celsius.

40. The sterilization indicator reading apparatus of embodiment 33, wherein the memory comprises instructions that when executed by the processor, causes the heating element to achieve a preset temperature in an incubation cycle.

41. The sterilization indicator reading apparatus of embodiment 40, wherein the memory comprises instructions that when executed by the processor, causes the display to show that the preset temperature is achieved in response to reaching the preset temperature.

42. The sterilization indicator reading apparatus of any of embodiments 1 to 41, wherein the memory comprises instructions that when executed by the processor, causes the processor to activate a fluorescence detection cycle to determine sterilization efficacy of the sterilization indicator based on a response to the excitation source.

43. The sterilization indicator reading apparatus of embodiment 42, wherein the activating the fluorescence detection cycle occurs in response to the sterilization indicator being present and activated or the preset temperature being achieved.

44. The sterilization indicator reading apparatus of embodiment 42, wherein activating the fluorescence detection cycle comprises:
activating the excitation source for a second time period,
receive a second reading from the color sensor corresponding to a second plurality of color channels, and
determine a fluorescence reading from the second plurality of color channels at the second time period.

45. The sterilization indicator reading apparatus of embodiment 44, wherein activating the fluorescence detection cycle further comprises:
acquiring a plurality of fluorescence readings;
determining whether the plurality of fluorescence readings is sufficient in number;
determining the sterilization efficacy based on the plurality of fluorescence readings.

46. The sterilization indicator reading apparatus of embodiment 45, wherein the fluorescence detection cycle indicates sterilization efficacy based on the plurality of fluorescence readings is not increasing.

47. The sterilization indicator reading apparatus of embodiment 45, wherein determining sterilization efficacy is based on the plurality of fluorescence readings increasing at a rate lower than a predetermined growth rate.

48. The sterilization indicator reading apparatus of embodiment 44, wherein activating the fluorescence detection cycle further comprises deactivating the excitation source based on the fluorescence reading being determinable.

49. The sterilization indicator reading apparatus of embodiment 44, wherein the memory comprises instructions that, when read by the processor, cause the controller circuit to activate the white LED of the sterilization indicator activation detection circuit for a first time period having a first duration, and activate the excitation source for a second time period having a second duration, wherein the first duration is less than a second duration of the second time period.

50. The sterilization indicator reading apparatus of embodiment 49, wherein the first time period has a first duration of no greater than 1 second, and the second time period has a second duration of greater than 1 second.

51. The sterilization indicator reading apparatus of embodiment 44, wherein activating the excitation source and the white LED occurs at the same time.

52. The sterilization indicator reading apparatus of embodiment 42, the memory comprises instructions that, when executed by the processor, cause the display to show a time remaining in response to activation of sterilization indicator and achieving the preset temperature.

53. The sterilization indicator reading apparatus of embodiment 42, wherein the memory comprises instructions that, when executed by the processor, cause the display to show a time remaining in response to activation of the fluorescence detection cycle.

54. The sterilization indicator reading apparatus of embodiment 53, wherein the time remaining is a prediction based on the plurality of fluorescence readings.

55. The sterilization indicator reading apparatus of embodiment 53, wherein the time remaining is paused if the sterilization indicator is removed.

56. The sterilization indicator reading apparatus of embodiment 53, wherein the memory comprises instructions that, when executed by the processor, cause the display to indicate a non-efficacious sterilization in response to the sterilization indicator being removed.

57. The sterilization indicator reading apparatus of any of embodiments 1 to 56, wherein the reading apparatus does not include filters external to the color sensor.

58. The sterilization indicator reading apparatus of any of embodiments 1 to 57, wherein the reading apparatus comprises at least 3 wells.

59. The sterilization indicator reading apparatus of embodiment 58, wherein the reading apparatus does not have more than 10 wells.

60. The sterilization indicator reading apparatus of embodiment 58, wherein the wells are arranged linearly across the x-dimension of the housing.

61. The sterilization indicator reading apparatus of embodiment 60, wherein the well axis of each well from a plurality of wells arranged linearly forms a plane that is parallel to the plane of the first printed circuit board.

62. The sterilization indicator reading apparatus of any of embodiments 1 to 61, wherein the housing has a translucent section therein.

63. The sterilization indicator reading apparatus of any of embodiments 1 to 62, wherein the top portion of the housing is removably detachable from the major side portion.

64. The sterilization indicator reading apparatus of any of embodiments 1 to 63, further comprising a spacing device that forms a portion of the well.

65. The sterilization indicator reading apparatus of embodiment 64, wherein the spacing device is configured to maintain positioning between elements on the first printed circuit board and the heater block.

66. The sterilization indicator reading apparatus of embodiment 65, wherein the spacing device comprises an aperture formed therein, wherein an aperture is dimensioned to secure the color sensor and positioned such that the color sensor would be horizontally aligned with the spores.

67. The sterilization indicator reading apparatus of embodiment 66, wherein the aperture is configured to focus fluoresced light from a larger surface area of the well to a smaller surface area of the color sensor.

68. The sterilization indicator reading apparatus of any of embodiments 1 to 67, wherein the excitation source produces ultraviolet (UV) light having a wavelength from 10 nm to 400 nm, preferably 300 nm to 400 nm.

69. The sterilization indicator reading apparatus of embodiment 68, wherein the excitation source is a UV LED.

70. The sterilization indicator reading apparatus of embodiment 68, wherein the excitation source is a UV laser.

71. A system comprising:
a sterilization indicator configured to emit a fluorescence signature in response to light;
the sterilization indicator reading apparatus of any of embodiments 1 to 70.

72. The system of embodiment 71, wherein a sterilization indicator configured to emit a fluorescence signature in response to ultraviolet light.

73. The system of embodiment 71, wherein the sterilization indicator comprises an indicator housing including:
a first portion, and
a second portion adapted to be coupled to the first portion, the second portion being movable with respect to the first portion, when coupled to the first portion between a first position and a second position; and
a container containing a medium and being dimensioned to be positioned in the indicator housing, at least a portion of the container being frangible, the container having a first state in which the container is intact when the second portion of the indicator housing is in the first position, and a second state in which the container is fractured when the second portion of the indicator housing is in the second position;
a first indicator chamber within the indicator housing in which the container is positioned when the container is in the first state; and
a second indicator chamber within the indicator housing in which the container and the medium are not positioned when the container is in the first state, and into which the medium moves when the container is in the second state, the second chamber comprising at least one source of biological activity that is not in fluid communication with the medium when the container is in the first state and that is in fluid communication with the medium when the container is in the second state.

74. A kit comprising:
a sterilization indicator configured to emit a fluorescence signature in response to light; and
the sterilization indicator reading apparatus of any of embodiments 1 to 70.

75. A method comprising:
providing a sterilization indicator having spores and a substance fluorescently responsive to the spore concentration and the spores are responsive to an environmental condition in a sterilizer;

providing a sterilization indicator reading apparatus of any of embodiments 1 to 70, comprising:
a housing comprising a top portion, a bottom portion, and a major side portion, a first section of the major side portion has an opacity of at least 99 percent as measured by ASTM D6216, a second section of the major side portion has an opacity of less than 99 percent (lower than first section) as measured by ASTM D6216;
a display contained within the housing such that a major side surface of the major side portion is continuous and the display is aligned with the first section, wherein the display has a brightness of at least 1 lumen, and at least 0.15 lumens when the light is transmitted through the major side portion of the housing;
allowing the reading apparatus to provide a timer sequence relating to an incubation cycle, fluorescence detection cycle, or combinations thereof to the display; reading the display through the housing.

76. The method of embodiment 75, further comprising:
allowing the reading apparatus to heat a heater block to a preset temperature and, upon achieving the preset temperature, allowing the reading apparatus to provide a temperature status to the display; and
reading the display through the housing.

77. The method of embodiment 75, further comprising:
wiping the major side portion across the first section and the second section without breaking a plane established by the major side portion.

78. The method of embodiment 75, further comprising:
sterilizing the sterilization indicator in a sterilizer.

79. A non-transitory computer-readable storage medium including instructions that, when processed by a computer, configure the computer to perform the method of embodiment 75.

80. A method comprising:
providing a sterilization reading apparatus of any of embodiments 1 to 70;
allowing the reading apparatus to achieve a preset temperature;
activating the sterilization indicator;
inserting the activated sterilization indicator into the well in response to a visual indication that the preset temperature was achieved;
receiving a determination whether the sterilization indicator has been activated; and
perform one or more operations in response to the determination.

81. The method of embodiment 80, further comprising pressing a button to indicate that the sterilization indicator has been activated after inserting the activated sterilization indicator.

82. A method comprising:
activating a white LED for a first time period;
receiving, by a color sensor, a response to the white LED from a sterilization indicator;
determining whether the sterilization indicator is activated based on the response;
activating an excitation source for a second time period;
receiving, by the color sensor, the fluorescent response to the excitation source from a sterilization indicator;
determining whether the sterilization indicator indicates a successful sterilization cycle based on the fluorescent response.

83. The method of embodiment 82, wherein the first time period is not overlapping with the second time period.

84. The method of embodiment 83, wherein the response is based on a purple color.

What is claimed is:

1. A sterilization indicator reading apparatus, comprising:
a housing comprising a top portion, a bottom portion, and a major side portion;
a well formed from a portion of the housing, accessible from the top portion, and oriented along a well axis from the top portion to the bottom portion, the well dimensioned to receive at least a portion of a sterilization indicator having spores that are responsive to an environmental condition in a sterilizer and a substance fluorescently responsive to spore concentration;
a heating element thermally coupled to a portion of the well;
a first printed circuit board that forms a first plane that is oriented parallel with the well axis, the first printed circuit board having disposed thereon;
a fluorescence excitation source configured to excite the fluorescently responsive substance of the sterilization indicator,
a white light source configured to direct white light into the sterilization indicator;
a color sensor positioned adjacent to the well; and
a controller circuit comprising:
a processor, wherein the heating element, the fluorescence excitation source, white light excitation source, and the color sensor are communicatively coupled to the processor; and
a memory communicatively coupled to the processor, wherein the memory comprises instructions that, when read by the processor, cause the controller circuit to activate the white light source for a first time period having a first duration, and activate the fluorescence excitation source for a second time period having a second duration, wherein the first duration is less than the second duration of the second time period.

2. The sterilization indicator reading apparatus of claim 1, the sterilization indicator has a vertical axis defined by a cap and a tip, and the vertical axis is parallel to a plane formed by the first printed circuit board.

3. The sterilization indicator reading apparatus of claim 1, further comprising a plurality of wells including a first well, wherein the first printed circuit board is continuous such that the excitation source, the white light source, and the color sensor of the first well is on the first printed circuit board as an excitation source, a white light source, and a color sensor of a second well.

4. The sterilization indicator reading apparatus of claim 1, further comprising a second printed circuit board having a display thereon, the second printed circuit board is parallel to the first printed circuit board.

5. The sterilization indicator reading apparatus of claim 1, wherein the memory comprises instructions that when executed by the processor, causes the processor to determine whether the sterilization indicator is activated based on a medium color of the sterilization indicator.

6. The sterilization indicator reading apparatus of claim 5, wherein, to determine whether the sterilization indicator is activated, the memory comprises instructions that when executed by the processor causes the processor to:
activate a fluorescence light source for the first time period;
activate the white light source for the second time period;

receive a first reading from the color sensor to determine presence of the sterilization indicator in the well; and receive a second reading from the color sensor to determine state of activation of the sterilization indicator.

7. The sterilization indicator reading apparatus of claim 6, wherein the memory comprises instructions that when executed by the processor, causes the processor to:

determine activation status of the sterilization indicator based on a first plurality of color channels.

8. The sterilization indicator reading apparatus of claim 7, wherein the memory comprises instructions that when executed by the processor, causes the processor to: deactivate the white light source in response to the sterilization indicator being activated.

9. The sterilization indicator reading apparatus of claim 8, wherein the color sensor is positioned to detect at least one of:

the sterilization indicator being positioned in the well with the medium not being present in a lower portion of an indicator chamber, and the sterilization indicator being positioned in the well with the medium being present in the lower portion of the indicator chamber.

10. The sterilization indicator reading apparatus of claim 1, further comprising a long pass filter disposed on the color sensor thereon.

11. The sterilization indicator reading apparatus of claim 1, further comprising a heater block forming a portion of the well, wherein the heating element is thermally coupled to the heater block.

12. The sterilization indicator reading apparatus of claim 1, wherein one or more indicator light emitting diodes distinct from a display are visible to a user, a first indicator light emitting diode indicates that the heating element is activated and a second indicator light emitting diode indicates whether a second temperature has been achieved.

13. The sterilization indicator reading apparatus of claim 12, wherein the memory comprises instructions that when executed by the processor, causes the heating element to achieve a preset temperature during an incubation cycle.

14. The sterilization indicator reading apparatus of claim 1, wherein the memory comprises instructions that when executed by the processor, causes the processor to activate a fluorescence detection cycle to determine sterilization efficacy of the sterilization indicator based on a response to the fluorescence excitation source.

15. The sterilization indicator reading apparatus of claim 14, wherein the memory comprises instructions that when executed by the processor, causes the processor to activate the fluorescence detection cycle by:

activating the fluorescence excitation source for a time period;

receive a reading from the color sensor corresponding to a plurality of color channels;

determine a fluorescence reading from the plurality of color channels at the time period;

acquiring a plurality of fluorescence readings; and determining the sterilization efficacy based on the plurality of fluorescence readings not increasing.

16. The sterilization indicator reading apparatus of claim 1, wherein the color sensor comprises an RGB color sensor.

17. A system comprising:

the sterilization indicator reading apparatus of claim 1; and a self-contained biological sterilization indicator configured to fit at least partially within a well of the sterilization indicator reading apparatus.

18. A sterilization indicator reading apparatus, comprising:

a housing comprising a top portion, a bottom portion, and a major side portion;

a well formed from a portion of the housing, accessible from the top portion, and oriented along a well axis from the top portion to the bottom portion, the well dimensioned to receive at least a portion of a sterilization indicator having spores that are responsive to an environmental condition in a sterilizer and a substance fluorescently responsive to spore concentration;

a heating element thermally coupled to a portion of the well; and a first printed circuit board that forms a first plane that is oriented parallel with the well axis, the first printed circuit board having disposed thereon;

a fluorescence excitation source configured to excite the fluorescently responsive substance of the sterilization indicator, a white light source configured to direct white light into the sterilization indicator;

a color sensor positioned adjacent to the well; and a controller circuit comprising:

a processor, and a memory communicatively coupled to the processor, the memory comprising instructions that when executed by the processor, causes the processor to:

determine whether the sterilization indicator is activated based on a medium color of the sterilization indicator;

activate a fluorescence light source for a first time period;

activate the white light source for a second time period;

receive a first reading from the color sensor to determine presence of the sterilization indicator in the well;

receive a second reading from the color sensor to determine state of activation of the sterilization indicator;

determine activation status of the sterilization indicator based on a first plurality of color channels; and deactivate the white light source in response to the sterilization indicator being activated, wherein the heating element, the fluorescence excitation source, white light excitation source, and a color sensor are communicatively coupled to the processor;

wherein the heating element, fluorescence excitation source, white light excitation source, and the color sensor are communicatively coupled to the processor.

19. A sterilization indicator reading apparatus, comprising:

a housing comprising a top portion, a bottom portion, and a major side portion;

a well formed from a portion of the housing, accessible from the top portion, and oriented along a well axis from the top portion to the bottom portion, the well dimensioned to receive at least a portion of a sterilization indicator having spores that are responsive to an environmental condition in a sterilizer and a substance fluorescently responsive to spore concentration;

a heating element thermally coupled to a portion of the well; and a first printed circuit board that forms a first plane that is oriented parallel with the well axis, the first printed circuit board having disposed thereon;
   a fluorescence excitation source configured to excite the fluorescently responsive substance of the sterilization indicator;
   a white light source configured to direct white light into the sterilization indicator;
   a color sensor, configured to detect at least one of:
      the sterilization indicator being positioned in the well with a medium not being present in a lower portion of an indicator chamber, and
      the sterilization indicator being positioned in the well with the medium being present in the lower portion of the indicator chamber; and
   a controller circuit comprising:
      a processor; and
      a memory communicatively coupled to the processor, the memory comprising instructions that when executed by the processor, causes the processor to:
         determine whether the sterilization indicator is activated based on a medium color of the sterilization indicator;
         activate a fluorescence light source for a first time period;
         activate the white light source for a second time period;
         receive a first reading from the color sensor to determine presence of the sterilization indicator in the well;
         receive a second reading from the color sensor to determine state of activation of the sterilization indicator;
         determine activation status of the sterilization indicator based on a first plurality of color channels; and
         deactivate the white light source in response to the sterilization indicator being activated, wherein the heating element, the fluorescence excitation source, white light excitation source, and a color sensor are communicatively coupled to the processor;
   wherein the heating element, the fluorescence excitation source, white light excitation source, and a color sensor are communicatively coupled to the processor.

* * * * *